United States Patent
Battrell et al.

(10) Patent No.: US 11,084,932 B2
(45) Date of Patent: Aug. 10, 2021

(54) PHENYLETHYNYLNAPHTHALENE DYES AND METHODS FOR THEIR USE

(71) Applicant: Sony Group Corporation, Tokyo (JP)

(72) Inventors: C. Frederick Battrell, Wenatchee, WA (US); Tracy Matray, Snohomish, WA (US); Hesham Sherif, Redmond, WA (US); Michael VanBrunt, Covington, WA (US)

(73) Assignee: Sony Group Corporation, Tokyo (JP)

( * ) Notice: Subject to any disclaimer, the term of this patent is extended or adjusted under 35 U.S.C. 154(b) by 0 days.

(21) Appl. No.: 15/553,546

(22) PCT Filed: Feb. 26, 2016

(86) PCT No.: PCT/US2016/019903
§ 371 (c)(1),
(2) Date: Aug. 24, 2017

(87) PCT Pub. No.: WO2016/138457
PCT Pub. Date: Sep. 1, 2016

(65) Prior Publication Data
US 2018/0237641 A1    Aug. 23, 2018

Related U.S. Application Data

(60) Provisional application No. 62/121,394, filed on Feb. 26, 2015.

(51) Int. Cl.
C09B 57/00 (2006.01)
C09B 69/00 (2006.01)
(Continued)

(52) U.S. Cl.
CPC ............ *C09B 57/00* (2013.01); *C07C 215/68* (2013.01); *C07F 9/094* (2013.01); *C07F 9/2429* (2013.01);
(Continued)

(58) Field of Classification Search
CPC ..... C09B 57/00; C09B 69/101; C09B 69/109; C09B 69/00; G01N 33/52; C07C 215/68; G03C 1/00; C09K 11/06
See application file for complete search history.

(56) References Cited

U.S. PATENT DOCUMENTS

| 4,450,305 A | 5/1984 | Kamhi |
| 4,476,229 A | 10/1984 | Fino et al. |

(Continued)

FOREIGN PATENT DOCUMENTS

| CN | 101137735 A | 3/2008 |
| CN | 102971283 A | 3/2013 |

(Continued)

OTHER PUBLICATIONS

Heterocyclic Chemistry, Heterocyclic Compounds, recovered from https://www2.chemistry.msu.edu /faculty/reusch/ virttxtjml/heterocy.htm on Apr. 3, 2017, pp. 1-14 (Year: 2017).*
Zaragoza Dorwald, Side Reactions in Organic Synthesis, 2005, WILEY-VCH Verlag GmbH & Co. KGaA, Weinheim, Preface. p. IX. (Year: 2005).*
Babitskaya et al., "Bromoacyl Analogues of Phosphatidylcholine with Intramolecular Fluorescence Quenching and Their Use as Substrates for Continuous Monitoring of Phospholipase A2 Activity," *Applied Biochemistry and Microbiology* 40(4):351-356, 2004.
Bergstrom et al., "A NaPi2b Antibody-Drug Conjugate Induces Durable Complete Tumor Regressions in Patient-Derived Xenograft Models of NSCLC," *IASLC 17th World Conference on Lung Cancer*, Vienna, Austria, Dec. 4-7, 2016. (8 pages).
Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015, 1 page.
Bergstrom et al., "Potent Promise," *Innovations in Pharmaceutical Technology* 49:16-20, 2014.
(Continued)

*Primary Examiner* — Sikarl A Witherspoon
(74) *Attorney, Agent, or Firm* — Seed IP Law Group LLP

(57) ABSTRACT

Compounds useful as fluorescent or colored dyes that enable visual detection of biomolecules and other analytes are disclosed. The compounds comprise a phenylethynylnapthalene moiety represented by the following structure (I):

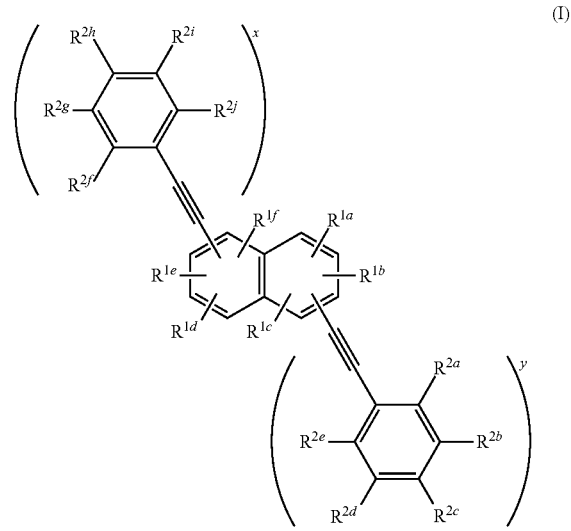

including salts thereof, wherein $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$, $R^{2f}$, $R^{2g}$, $R^{2h}$, $R^{2i}$, $R^{2j}$, x and y are as defined herein. Methods associated with preparation and use of such compounds for visually detecting a biomolecule are also provided.

20 Claims, 1 Drawing Sheet

(51) Int. Cl.

| | | |
|---|---|---|
| G01N 33/00 | (2006.01) | |
| C07C 215/00 | (2006.01) | |
| G01N 33/52 | (2006.01) | |
| C07F 9/09 | (2006.01) | |
| C07F 9/24 | (2006.01) | |
| C07C 215/68 | (2006.01) | |
| G03C 1/00 | (2006.01) | |
| C09B 23/14 | (2006.01) | |
| C09B 69/10 | (2006.01) | |
| C07F 9/572 | (2006.01) | |

(52) U.S. Cl.
CPC ............ *C07F 9/572* (2013.01); *C09B 23/141* (2013.01); *C09B 69/00* (2013.01); *C09B 69/101* (2013.01); *C09B 69/109* (2013.01); *G01N 33/52* (2013.01); *G03C 1/00* (2013.01)

(56) References Cited

U.S. PATENT DOCUMENTS

| | | | |
|---|---|---|---|
| 5,053,054 | A | 10/1991 | Kirchanski et al. |
| 5,268,486 | A | 12/1993 | Waggoner et al. |
| 5,318,894 | A | 6/1994 | Pugia |
| 6,140,480 | A | 10/2000 | Kool |
| 6,171,859 | B1 | 1/2001 | Hermstadt et al. |
| 6,218,108 | B1 | 4/2001 | Kool |
| 6,479,650 | B1 | 11/2002 | Kool |
| 6,627,400 | B1 | 9/2003 | Singh et al. |
| 6,670,193 | B2 | 12/2003 | Kool |
| 6,716,452 | B1 | 4/2004 | Piccariello et al. |
| 6,852,709 | B2 | 2/2005 | Leong et al. |
| 7,060,708 | B2 | 6/2006 | Piccariello et al. |
| 7,172,907 | B2 | 2/2007 | Chen et al. |
| 7,423,133 | B2 | 9/2008 | Kool et al. |
| 7,667,024 | B2 | 2/2010 | Mao et al. |
| 7,897,684 | B2 | 3/2011 | Bazan et al. |
| 8,217,389 | B2 | 7/2012 | Nakano et al. |
| 8,349,308 | B2 | 1/2013 | Yurkovetskiy et al. |
| 8,431,545 | B2 | 4/2013 | Kataoka et al. |
| 8,632,947 | B2 | 1/2014 | Bentley et al. |
| 8,802,738 | B2 | 8/2014 | Emrick |
| 9,085,799 | B2 | 7/2015 | Bazan et al. |
| 9,150,782 | B2 | 10/2015 | Lee et al. |
| 9,400,273 | B1 | 7/2016 | Liu et al. |
| 9,545,447 | B2 | 1/2017 | Wooley et al. |
| 9,687,291 | B2 | 6/2017 | Shimizu et al. |
| 9,689,877 | B2 * | 6/2017 | Matray ............... C07F 9/093 |
| 9,765,220 | B2 | 9/2017 | Matray et al. |
| 9,851,359 | B2 | 12/2017 | Matray et al. |
| 9,884,070 | B2 | 2/2018 | Denardo et al. |
| 9,913,992 | B2 | 3/2018 | Demarest et al. |
| 9,939,454 | B2 | 4/2018 | Dzubay et al. |
| 10,036,754 | B2 | 7/2018 | Matray et al. |
| 10,435,563 | B2 | 10/2019 | Matray et al. |
| 10,709,791 | B2 | 7/2020 | Stayton et al. |
| 10,865,310 | B2 | 12/2020 | Matray et al. |
| 10,866,244 | B2 | 12/2020 | Matray et al. |
| 10,954,391 | B2 | 3/2021 | Matray et al. |
| 2002/0099013 | A1 | 7/2002 | Piccariello et al. |
| 2003/0054361 | A1 | 3/2003 | Heller |
| 2003/0207208 | A1 | 11/2003 | Uenishi |
| 2004/0014981 | A1 | 1/2004 | Lugade et al. |
| 2004/0138467 | A1 | 7/2004 | French et al. |
| 2004/0186278 | A1 | 9/2004 | Chen et al. |
| 2004/0224372 | A1 | 11/2004 | Li et al. |
| 2005/0054024 | A1 | 3/2005 | Lawrence |
| 2005/0123935 | A1 | 6/2005 | Haugland et al. |
| 2006/0008822 | A1 | 1/2006 | Manoharan et al. |
| 2006/0063186 | A1 | 3/2006 | Benson et al. |
| 2007/0042398 | A1 | 2/2007 | Peng et al. |
| 2007/0077549 | A1 | 4/2007 | Buller et al. |
| 2007/0148094 | A1 | 6/2007 | Uzgiris et al. |
| 2007/0269902 | A1 | 11/2007 | Beechem et al. |
| 2008/0227939 | A1 | 9/2008 | Mizoshita et al. |
| 2009/0253792 | A1 | 10/2009 | Mickle et al. |
| 2009/0299070 | A1 * | 12/2009 | Berens ............... H01L 51/0058 546/56 |
| 2010/0039684 | A1 * | 2/2010 | Kolb ..................... G03F 7/038 359/3 |
| 2010/0092386 | A1 | 4/2010 | Segev |
| 2010/0192312 | A1 | 8/2010 | Cremer et al. |
| 2012/0116079 | A1 | 5/2012 | Lukhtanov et al. |
| 2012/0126175 | A1 | 5/2012 | Ueno et al. |
| 2013/0059343 | A1 | 3/2013 | Cheung |
| 2013/0102021 | A1 | 4/2013 | Beacham et al. |
| 2013/0119363 | A1 * | 5/2013 | Sasaki ..................... C07C 43/225 257/40 |
| 2013/0137755 | A1 | 5/2013 | Segev |
| 2013/0202536 | A1 | 8/2013 | Mustaev et al. |
| 2013/0244891 | A1 | 9/2013 | Waggoner et al. |
| 2015/0011614 | A1 | 4/2015 | Eder et al. |
| 2015/0159198 | A1 | 6/2015 | McGall et al. |
| 2015/0232615 | A1 | 8/2015 | Kwiatkowski |
| 2015/0258217 | A1 | 9/2015 | Caravan et al. |
| 2016/0039850 | A1 | 2/2016 | Segev |
| 2016/0176903 | A1 | 6/2016 | Segev |
| 2016/0208100 | A1 | 7/2016 | Matray et al. |
| 2016/0264737 | A1 | 9/2016 | Bartholomew et al. |
| 2016/0327859 | A1 | 11/2016 | Idei et al. |
| 2016/0341736 | A1 | 11/2016 | Matray et al. |
| 2016/0347907 | A1 | 12/2016 | Dose |
| 2017/0292957 | A1 | 10/2017 | Matray et al. |
| 2017/0326233 | A1 | 11/2017 | Demeule et al. |
| 2018/0065998 | A1 | 3/2018 | Battrell et al. |
| 2018/0079909 | A1 | 3/2018 | Matray et al. |
| 2018/0163052 | A1 | 6/2018 | Matray et al. |
| 2018/0164322 | A1 | 6/2018 | Matray et al. |
| 2018/0237641 | A1 | 8/2018 | Matray et al. |
| 2019/0016898 | A1 | 1/2019 | Matray et al. |
| 2019/0136065 | A1 | 5/2019 | Singh et al. |
| 2019/0144678 | A1 | 5/2019 | Matray et al. |
| 2019/0153232 | A1 | 5/2019 | Matray et al. |
| 2019/0177549 | A1 | 6/2019 | Matray et al. |
| 2019/0300716 | A1 | 10/2019 | Matray et al. |
| 2020/0109287 | A1 | 4/2020 | Matray et al. |
| 2020/0222554 | A1 | 7/2020 | Matray et al. |
| 2020/0284798 | A1 | 9/2020 | Matray et al. |
| 2020/0353089 | A1 | 11/2020 | Matray |
| 2020/0353094 | A1 | 11/2020 | Matray |
| 2020/0360526 | A1 | 11/2020 | Matray |
| 2020/0392345 | A1 | 12/2020 | Matray et al. |
| 2021/0032277 | A1 | 2/2021 | Matray et al. |
| 2021/0032474 | A1 | 2/2021 | Matray et al. |

FOREIGN PATENT DOCUMENTS

| | | | |
|---|---|---|---|
| CN | 106589005 | A | 4/2017 |
| DE | 197 17 904 | A1 | 10/1998 |
| EP | 0 708 837 | A1 | 5/1996 |
| EP | 1 650 269 | A2 | 4/2006 |
| EP | 1 655 317 | A1 | 5/2006 |
| EP | 2 336 785 | A1 | 9/2011 |
| GB | 2 456 298 | A | 7/2009 |
| GB | 2554666 | A | 4/2018 |
| JP | 4-282391 | A | 10/1992 |
| JP | 2008-510041 | A | 4/2008 |
| JP | 2008-535945 | A | 9/2008 |
| JP | 2009-519595 | A | 5/2009 |
| JP | 2010-508295 | A | 3/2010 |
| SU | 1121931 | A | 4/1988 |
| WO | 93/06482 | A1 | 4/1993 |
| WO | 94/13688 | A1 | 6/1994 |
| WO | 95/02700 | A1 | 1/1995 |
| WO | 01/69254 | A2 | 9/2001 |
| WO | 01-83502 | A1 | 11/2001 |
| WO | 02/22883 | A1 | 3/2002 |
| WO | 02/36832 | A2 | 5/2002 |
| WO | 2006/020947 | A2 | 2/2006 |
| WO | 2006/099050 | A2 | 9/2006 |
| WO | 2009/015467 | A1 | 2/2009 |
| WO | 2010/026957 | A1 | 3/2010 |
| WO | 2013/012687 | A2 | 1/2013 |
| WO | 2014/043289 | A2 | 3/2014 |

(56) References Cited

FOREIGN PATENT DOCUMENTS

| | | |
|---|---|---|
| WO | 2014/102803 A1 | 7/2014 |
| WO | 2014/147642 A1 | 9/2014 |
| WO | 2014/159392 A1 | 10/2014 |
| WO | 2015/027176 A1 | 2/2015 |
| WO | 2015/109136 A2 | 7/2015 |
| WO | 2015/115415 A1 | 8/2015 |
| WO | 2016/138461 A1 | 9/2016 |
| WO | 2016/183185 A1 | 11/2016 |
| WO | 2017/173348 A1 | 10/2017 |
| WO | 2017/173355 A1 | 10/2017 |
| WO | 2017/177065 A2 | 10/2017 |
| WO | 2018/060722 A1 | 4/2018 |
| WO | 2019/071208 A1 | 4/2019 |
| WO | 2020/210689 A1 | 10/2020 |
| WO | 2020/210692 A1 | 10/2020 |
| WO | 2020/210694 A1 | 10/2020 |
| WO | 2021/062176 A2 | 4/2021 |

OTHER PUBLICATIONS

Bergstrom et al., "XMT-1522 induces tumor regressions in preclinical models representing HER2-positive and HER2 low-expressing breast cancer," Mersana Therapeutics, Abstract P4-14-28, 2015, 1 page.
Chong et al., "Oxygen Quenching of Pyrene-Lipid Fluorescence in Phosphatidylcholine Vesicles—A Probe for Membrane Organization," *Biophys. J.* 47:613-621, 1985.
Liu et al., "Detection of prostate-specific membrane antigen on HUVECs in response to breast tumor-conditioned medium," *International Journal of Oncology* 38:1349-1355, 2011.
Liu et al., "DNA-Based Micelles: Synthesis, Micellar Properties and Size-Dependent Cell Permeability," *Chem. Eur. J.* 16:3791-3797, 2010. (14 Pages).
Mersana Therapeutics, URL= http://www.mersana.com, download date Jan. 3, 2019, 9 pages.
Molotkovsky et al., "Perylenoyl- and Anthrylvinyl-Labeled Lipids as Membrane Probes," *Biochimica et Biophysica Acta* 778:281-288, 1984.
Pownall et al., "Kinetics of Spontaneous and Plasma-Stimulated Sphingomyelin Transfer," *Biochimica et Biophysica Acta* 712:169-176, 1982.
Wilson et al., "Oligodeoxyfluorosides: Strong Sequence of Dependence of Fluorescence Emission," *Tetrahedron* 63(17):3427-3433, 2007. (18 Pages).
Yurkovetskiy et al., "Advantages of Polyacetal Polymer-based Antibody Drug Conjugates: Application to Low Expression Targets," Mersana Therapeutics, technical paper #2645, 2014, 1 page.
CAPLUS Accession No. 1975:171341, Holy, "Nucleic acid components and their analogs. CLXXII. Aliphatic analogs of nucleosides, nucleotides, and oligonucleotides," *Collection of Czechoslovak Chemical Communications* 40(1):187-214, 1975. (1 page).
"What is an Analyte?," Google Search, dated Mar. 22, 2018, retrieved from https://www.google.com/search?q=what+is+an+analyte&rlz=1C1GCEB_enUS775US775&oq=what+is+an+analyte&aqs=chrome..69i57j0l5.32321j0j7&s . . . 2 pages.
Arian et al., "1,9-Dialkoxyanthracene as a $^1O_2$-Sensitive Linker," *J. Am. Chem. Soc.* 133:3972-3980, 2011.
Becker et al., "New Thermotropic Dyes Based on Amino-Substituted Perylendicarboximides," *Chem. Eur. J.* 6(21):3984-3990, 2000.
Braeckmans et al., "Three-Dimensional Fluorescence Recovery after Photobleaching with the Confocal Scanning Laser Microscope," *Biophysical Journal* 85:2240-2252, 2003.
Braga et al., "Intracellular Macromolecular Mobility Measured by Fluorescence Recovery after Photobleaching with Confocal Laster Scanning Microscopes," *Molecular Biology of the Cell* 15:4749-4760, 2004.
Brinkley, "A Brief Survey of Methods for Preparing Protein Conjugates with Dyes, Haptens, and Cross-Linking Reagents," *Bioconjugate Chem* 3:2-13, 1992.
Dai et al., "DNA-polyfluorophore excimers as sensitive reporters for esterases and lipases," *Chem. Commun.* 46:1221-1223, 2010.
Divittorio et al., "Synthetic peptides with selective affinity for apoptotic cells," *Organic & Biomolecular Chemistry* 4(10):1966-2006.
Gao et al., "Libraries of Composite Polyfluors Built from Fluorescent Deoxyribosides," *Journal of the American Chemical Society* 124(39):11590-11591, 2002.
Gao et al., "Modified DNA Analogues That Sense Light Exposure with Color Changes," *J. Am. Chem. Soc.* 126:12748-12749, 2004.
Gordon et al., "Analysis of Simulated and Experimental Fluorescence Recovery After Photobleaching. Data for Two Diffusing Components," *Biophysical Journal* 68:766-778, 1995.
Hanhela et al., "Synthesis and Evaluation of Fluorescent Materials for Colour Control of Peroxyolate Chemiluminescene. III Yellow and Red Fluorescent Emitters," *Aust. J. Chem.* 34:1701-1717, 1981.
Haraguchi et al., "Live Cell Imaging: Approaches for Studying Protein Dynamics in Living Cells," *Cell Structure and Function* 27:333-334, 2002.
Koo et al., "Fluorescent DNA chemosensors: identification of bacterial species by their volatile metabolites," *Chem. Commun.* 47:11435-11437, 2011.
Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.
Nussbaumer et al., "Amplification of Chirality by Supramolecular Polymerization of Pyrene Oligomers," *Angew. Chem. Int. Ed.* 50:5490-5494, 2011.
PubChem, "US20100012929A1-20100121-C00010_4," SID No. 140452858, retrieved Mar. 29, 2016 from URL https://pubchem.ncbi.nlm.nih.gov/substance/140452858, 6 pages.
Wang et al., "Cruciforms: Assembling Single Crystal Micro- and Nanostructures from One to Three Dimensions and Their Applications in Organic Field-Effect Transistors," *Chem. Mater.* 21:2840-2845, 2009.
Wang et al., "DNA Polyfluorophores for Real-Time Multicolor Tracking of Dynamic Biological Systems," *Angew. Chem. Int. Ed.* 51:7176-7180, 2012.
Wilson et al., "Efficient Quenching of Oligomeric Fluorophores on a DNA Backbone," *J. Am. Chem. Soc.* 129:15426-15427, 2007.
RN 230952-79-1, Registry Database Compound (1999).
Kozma et al., "Fluorescent Ligands for Adenosine Receptors," *Bioorganic & Medicinal Chemistry Letters* 23: 26-36, 2013.
Leung et al., "7-Amino-4-Methyl-6-Sulfocoumarin-3-Acetic Acid: A Novel Blue Fluorescent Dye for Protein Labeling," *Bioorganic & Medicinal Chemistry Letters* 9: 2229-2232, 1999.
Petreus et al., "Polyester imides containing main-chain phosphorus," *Revue Roumaine de Chimie* 34(8):971-978, 1994 (with English Abstract) (9 pages).
Singh et al., "Multiplexed measurement of membrane protein populations," Caplus 2003:769075, 2003. (2 pages).
U.S. Appl. No. 16/639,496, filed Feb. 14, 2020.
U.S. Appl. No. 16/639,499, filed Feb. 14, 2020.
U.S. Appl. No. 16/763,922, filed May 13, 2020.
Daniels et al., "Fluorescence of the Purine and Pyrimidine Bases of the Nucleic Acids in Neutral Aqueous Solution at 300°K," *Science* 171(3972):675-677, 1971.
Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.
Jain et al. "Current ADC Linker Chemistry," *Pharm. Res.* 32:3526-3540, 2015.
Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.
U.S. Appl. No. 16/771,185, filed Jun. 9, 2020.
U.S. Appl. No. 16/934,912, filed Jul. 21, 2020.
U.S. Appl. No. 16/961,403, filed Jul. 10, 2020.
U.S. Appl. No. 16/961,414, filed Jul. 10, 2020.
U.S. Appl. No. 16/961,429, filed Jul. 10, 2020.
U.S. Appl. No. 16/982,341, filed Sep. 18, 2020.

(56) References Cited

OTHER PUBLICATIONS

U.S. Appl. No. 16/982,355, filed Sep. 18, 2020.
Avirah et al., "Infrared Absorbing Croconaine Dyes: Synthesis and Metal Ion Binding Properties," *J. Org. Chem.* 73(1):274-279, 2008.
Chattopadhyay et al., "Brilliant Violet Fluorophores: A New Class of Ultrabright Fluorescent Compounds for Immunofluorescence Experiments," *Cytometry Part A* 81A:456-466, 2012.
Cuppoletti et al., "Oligomeric fluorescent labels for DNA," *Bioconjug. Chem.* 16(3):528-534, 2005.
Dubrovsky, "Semiconductor nanoparticles as reporters in multiplexed immunoassay and cell analysis," *International Journal of Nanoscience* 8(1 & 2):163-167, 2009.
Li et al., "Polymeric Drugs: Advances in the development of pharmacologically active polymers," *Journal of Controlled Release* 219:360-382, 2015.
Li et al., "Responsive nanogel-based dual fluorescent sensors for temperature and $Hg^{2+}$ ions with enhanced detection sensitivity," *J. Mater. Chem.* 20:10716-10723, 2010.
Luo et al., "Sensitive and rapid quantification of C-reactive protein using quantum dot-labeled microplate immunoassay," *Journal of Translational Medicine* 10(24):1-9, 2012.
Paris et al., "Probing DNA sequences in solution with a monomer-excimer fluorescence color change," *Nucleic Acids Research* 26(16):3789-3793, 1998.
Ren et al., "An Antisense Oligodeoxynucleotide-Doxorubicin Conjugate: Preparation and Its Reversal Multidrug Resistance of Human Carcinoma Cell Line In Vitro," *Nucleosides, Nucleotides & Nucleic Acids* 23(10):1595-1607, 2004.
Stewart et al., "The Fluorescence of a Chelating Two-Photon-Absorbing Dye is Enhanced with the Addition of Transition Metal Ions but Quenched in the Presence of Acid," *Proc. of SPIE* 9939:993904, 2016 (10 pages).
Stuart et al., "Site-Specific DNA-Doxorubicin Conjugates Display Enhanced Cytotoxicity to Breast Cancer Cells," *Bioconjugate Chemistry* 25:406-413, 2014.
Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 25, 2010, 23 pages).
Tram et al., "Oligonucleotide Labeling Using BODIPY Phosphoramidite," *Nucleosides, Nucleotides & Nucleic Acids* 30(1):1-11, 2011.
Zhang et al., "FRET Imaging of Enzyme-Responsive HPMA Copolymer Conjugate," *Macromolecular Bioscience* 17:1600215, 2017 (8 pages).
Beaucage et al., "The Functionalization of Oligonucleotides Via Phosphoramidite Derivatives," *Tetrahedron* 49(10):1925-1963, 1993.
Doi et al., "Hetero-Selective DNA-Like Duplex Stabilized by Donor-Acceptor Interactions," *Chem. Eur. J.* 21:15974-15980, 2015.
Johansson, "Choosing Reporter-Quencher Pairs for Efficient Quenching Through Formation of Intramolecular Dimers," *Methods in Molecular Biology* 335:17-29, 2006.
Saito et al., "Dual-labeled oligonucleotide probe for sensing adenosine via FRET: A novel alternative to SNPs genotyping," *Chem. Commun.*:2133-2135, 2007.

\* cited by examiner

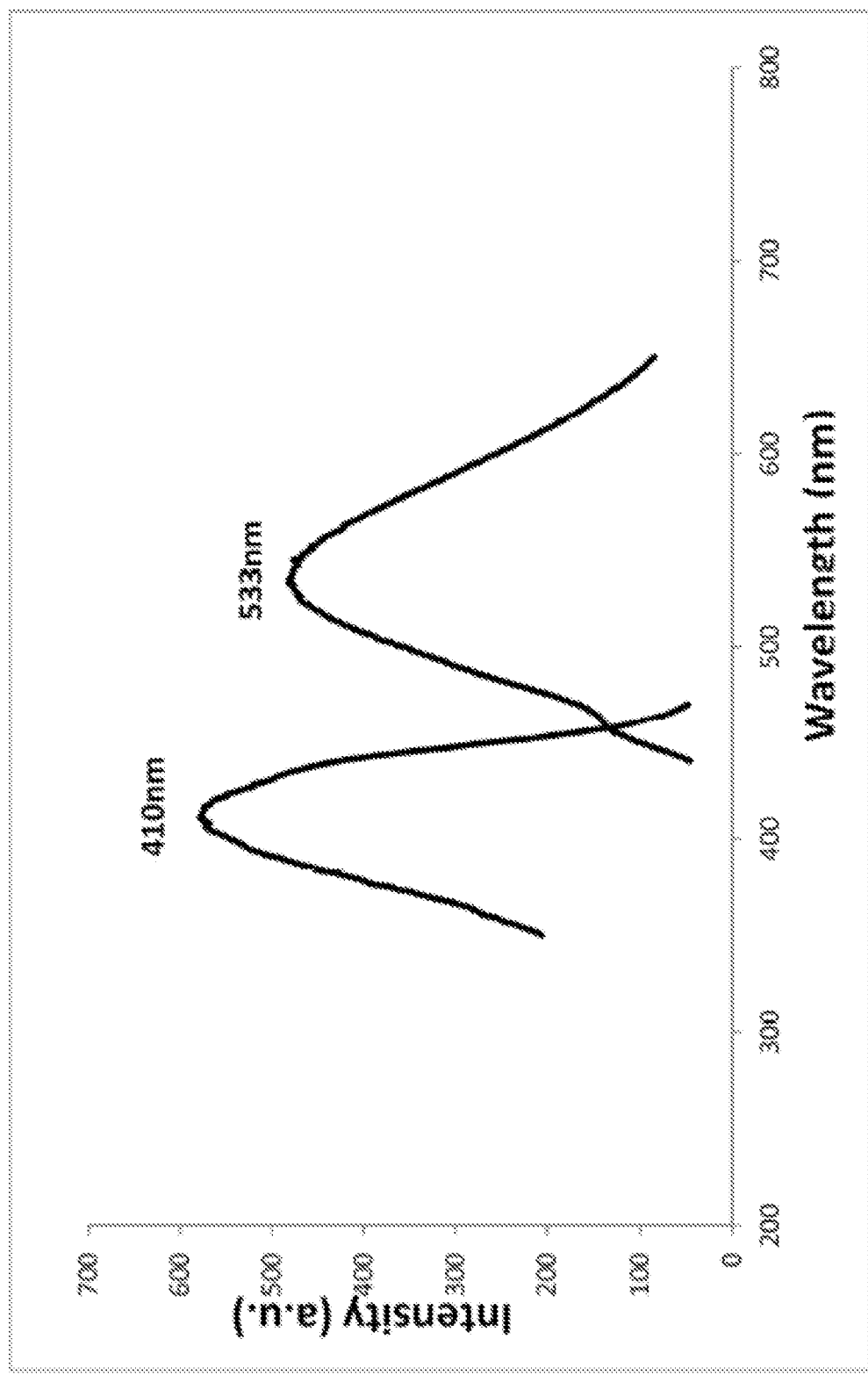

PHENYLETHYNYLNAPHTHALENE DYES AND METHODS FOR THEIR USE

BACKGROUND

Field

The present invention is directed to novel fluorescent or colored dyes comprising a phenylethynylnapthalene moiety and methods for their preparation and use in various analytical methods.

Description of the Related Art

There is a continuous and expanding need for rapid, highly specific methods of detecting and quantifying chemical, biochemical and biological substances as analytes in research and diagnostic mixtures. Of particular value are methods for measuring small quantities of nucleic acids, peptides, saccharides, pharmaceuticals, metabolites, microorganisms, ions, and other materials of diagnostic value. Examples of such materials include narcotics and poisons, drugs administered for therapeutic purposes, hormones, pathogenic microorganisms and viruses, peptides, e.g., antibodies and enzymes, and nucleic acids, particularly those implicated in disease states.

The presence of a particular analyte can often be determined by binding methods that exploit the high degree of specificity that characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which is attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding affinities of those materials. The label should give a highly characteristic signal, and should be rarely, and preferably never, found in nature. The label should be stable and detectable in aqueous systems over periods of time ranging up to months. Detection of the label is preferably rapid, sensitive, and reproducible without the need for expensive, specialized facilities or the need for special precautions to protect personnel. Quantification of the label is preferably relatively independent of variables such as temperature and the composition of the mixture to be assayed.

A wide variety of labels have been developed, each with particular advantages and disadvantages. For example, radioactive labels are quite versatile, and can be detected at very low concentrations. However, such labels are expensive, hazardous, and their use requires sophisticated equipment and trained personnel. Thus, there is wide interest in non-radioactive labels, particularly in labels that are observable by spectrophotometric, spin resonance, and luminescence techniques, and reactive materials, such as enzymes that produce such molecules.

Labels that are detectable using fluorescence spectroscopy are of particular interest because of the large number of such labels that are known in the art. Moreover, the literature is replete with syntheses of fluorescent labels that are derivatized to allow their attachment to other molecules, and many such fluorescent labels are commercially available.

Cyanine dyes have been widely used for labeling biomolecules including antibodies, DNA probes, avidin, streptavidin, lipids, biochemical analogs, peptides, and drugs, as well as for a variety of applications including DNA sequencing, DNA microarray, western blotting, flow cytometry analysis, and protein microarrays, to name a few. Scientists favor using cyanine dyes in biological applications because, among other reasons, cyanine dyes 1) are biocompatible; 2) have high molar absorptivity (c.a. $10^5$ $M^{-1}$ $cm^{-1}$); 3) are readily modified to match a wide range of desired excitation and detection wavelengths (e.g., about 500 to about 900 nm); 4) are capable of incorporating water-soluble groups and linking groups; 5) and possess favorable fluorescence properties. In particular, Cy2 conjugates, with a maximum adsorption/excitation around 492 nm and emission around 510 nm, in the green region of the visible spectrum, are commonly used as an alternative to FITC due to reduced sensitivity to pH changes. However, the low fluorescence quantum yield, short fluorescence lifetime, propensity to photobleach, and poor chemical stability of Cy2 has limited its use in chemical and life sciences.

There is thus a need in the art for water soluble dyes and biomarkers that permit visual or fluorescent detection of biomolecules without prior illumination or chemical or enzymatic activation. Ideally, such dyes and biomarkers should be intensely colored or fluorescent and should be available in a variety of colors and fluorescent wavelengths. The present invention fulfills this need and provides further related advantages.

BRIEF SUMMARY

In brief, the present invention is generally directed to compounds useful as water soluble, fluorescent or colored dyes and probes that enable visual detection of biomolecules and other analytes, as well as reagents for their preparation. Methods for visually detecting a biomolecule and for determining the size of a biomolecule are also described. The water soluble, fluorescent or colored dyes of the invention are intensely colored and/or fluorescent and can be readily observed by visual inspection or other means. In some embodiments the compounds may be observed without prior illumination or chemical or enzymatic activation. Advantageously, embodiments of the dyes have a maximum excitation wavelength ranging from about 400 nm to about 420 nm and a maximum emission wavelength ranging from about 520 nm to about 540 nm. For example, in certain embodiment the dyes have a maximum excitation wavelength at about 410 nm and a maximum emission wavelength at about 533 nm. The dyes are thus ideal for use in various analytical methods. By appropriate selection of the dye, as described herein, visually detectable biomolecules of a variety of colors may be obtained.

Accordingly, in one embodiment a compound having the following structure (I) is provided:

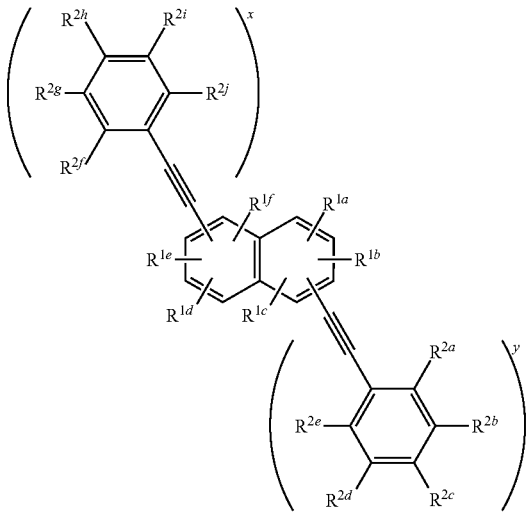

(I)

or a salt thereof, wherein $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$, $R^{2f}$, $R^{2g}$, $R^{2h}R^{2i}$, $R^{2j}$, x and y are as defined herein.

In another embodiment, a method for staining a sample is provided; the method comprises adding to said sample a representative compound as described herein in an amount sufficient to produce an optical response when said sample is illuminated at an appropriate wavelength.

In still other embodiments, the present disclosure provides a method for visually detecting a biomolecule, comprising:

(a) providing a representative compound described herein; and (b) detecting the compound by its visible properties.

Other disclosed methods include a method for visually detecting a biomolecule, the method comprising:

(a) admixing any of the disclosed compounds with one or more biomolecules; and (b) detecting the compound by its visible properties.

Other embodiments are directed to a composition comprising any one of the disclosed compounds and one or more biomolecules. Use of such composition in analytical methods for detection of the one or more biomolecules is also provided.

These and other aspects of the invention will be apparent upon reference to the following detailed description.

DESCRIPTION OF THE DRAWINGS

In the figures, identical reference numbers identify similar elements. The sizes and relative positions of elements in the figures are not necessarily drawn to scale and some of these elements may be enlarged and positioned to improve figure legibility. Further, the particular shapes of the elements as drawn are not intended to convey any information regarding the actual shape of the particular elements, and have been solely selected for ease of recognition in the figures.

The figure depicts a UV spectrum of an exemplary compound. The exemplary compound shows a maximum excitation wavelength at about 410 nm and a maximum emission wavelength at about 533 nm.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ group.

"Carboxy" refers to the —CO$_2$H group.

"Cyano" refers to the —CN group.

"Formyl" refers to the —C(═O)H group.

"Hydroxy" or "hydroxyl" refers to the —OH group.

"Imino" refers to the ═NH group.

"Nitro" refers to the —NO$_2$ group.

"Oxo" refers to the ═O substituent group.

"Sulfhydryl" refers to the —SH group.

"Thioxo" refers to the ═S group.

"Alkyl" refers to a straight or branched hydrocarbon chain group consisting solely of carbon and hydrogen atoms, which is saturated or unsaturated (i.e., contains one or more double and/or triple bonds). In some embodiments, alkyl groups have from one to twelve carbon atoms (C$_1$-C$_{12}$ alkyl), preferably one to eight carbon atoms (C$_1$-C$_8$ alkyl) or one to six carbon atoms (C$_1$-C$_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group is optionally substituted.

"Alkylene" or "alkylene chain" refers to a straight or branched divalent hydrocarbon chain linking the rest of the molecule to a substituent group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the substituent group through a single or double bond. The points of attachment of the alkylene chain to the rest of the molecule and to the substituent group can be through one carbon or any two carbons within the chain. "Heteroalkylene" refers to an alkylene in which at least one carbon-carbon bond has been replaced with a carbon heteroatom (e.g., N, S, or O) bond. The heteroatom may be at any position in the heteroalkylene, including a terminal position such that the heteroatom links the heteroalkylene to the reminder of the molecule. Unless stated otherwise specifically in the specification, an alkylene chain is optionally substituted.

"Aminoalkylene" refers to an alkylene, as defined, comprising one or more amino substituents. Unless stated otherwise specifically in the specification, aminoalkylene groups are optionally substituted.

"Alkoxy" refers to a group of the formula —OR$_a$ where R$_a$ is an alkyl group as defined above containing one to twelve carbon atoms. A "hydroxylalkoxy" is an alkoxy moiety comprising at least one hydroxyl substituent. An "aminoalkoxy" is an alkoxy moiety comprising at least one amino substituent. Unless stated otherwise specifically in the specification, alkoxy, hydroxylalkoxy and/or aminoalkoxy groups are optionally substituted.

"Alkylamino" refers to a group of the formula —NHR$_a$ or —NR$_a$R$_a$ where each R$_a$ is, independently, an alkyl group as defined above containing one to twelve carbon atoms. Unless stated otherwise specifically in the specification, an alkylamino group is optionally substituted.

"Alkylcarbonyl" refers to an alkyl group as defined above, which is connected to the remainder of the molecule through a carbonyl (C=O) linkage. Unless stated otherwise specifically in the specification, an alkylcarbonyl group is optionally substituted.

"Alkylcarbonyloxy" refers to a group of the formula RC(=O)O—, wherein R is an alkyl group as defined above. Unless stated otherwise specifically in the specification, an alkylcarbonyloxy group is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one (i.e., a "polyalkylether"). For example, polyethylene glycol (PEG), which is a polyalkylether, is included within the meaning of alkylether. "Hydroxylpolyalkylether" refers to a polyalkylether comprising one or more hydroxyl substituents. "Aminopolyalkylether" refers to a polyalkylether comprising one or more amino substituents. Unless stated otherwise specifically in the specification, an alkylether, polyalkylether, hydroxylpolyalkylether and/or aminopolyalkylether group is optionally substituted.

"Alkylenether" refers to an alkylene group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylenethers include at least one carbon oxygen bond, but may include more than one (i.e., a "polyalkylenether"). PEG linking groups are examples of polyalkylenethers. "Hydroxylpolyalkylenether" refers to a polyalkylenether comprising at least on hydroxyl substituent.

"Aminopolyalkylenether" refers to a polyalkylenether comprising at least one amino (including alkylamino, arylamino and aralkylamino) substituent. Unless stated otherwise specifically in the specification, alkylenether, polyalkylenether, hydroxylpolyalkylenether and aminopolyalkylenether groups, are optionally substituted.

"Aryl" refers to a carbocyclic ring system group comprising 6 to 18 carbon atoms and at least one carbocyclic aromatic ring. For purposes of this invention, the aryl group may be a monocyclic, bicyclic, tricyclic or tetracyclic ring system, which may include fused or bridged ring systems. Aryl groups include, but are not limited to, aryl groups derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl groups that are optionally substituted.

"Arylamino" refers to a group of the formula —NR$_a$R$_b$ where R$_a$ is aryl, as defined above, and R$_b$ is H, alkyl, as defined above containing one to twelve carbon atoms, or aryl as defined above. Unless stated otherwise specifically in the specification, an arylamino group is optionally substituted.

"Aryloxy" refers to a group of the formula —OR$_a$, where R$_a$ is an aryl moiety as defined above, for example phenoxy and the like. Unless stated otherwise specifically in the specification, an aryloxy group is optionally substituted.

"Arylcarbonyl" refers to an aryl group as defined above, which is connected to the remainder of the molecule through a carbonyl (C=O) linkage. Unless stated otherwise specifically in the specification, an arylcarbonyl group is optionally substituted.

"Arylcarbonyloxy" refers to a group of the formula RC(=O)O—, wherein R is an aryl group as defined above. Unless stated otherwise specifically in the specification, an arylcarbonyloxy group is optionally substituted.

"Aralkyl" refers to a group of the formula —R$_b$—R$_c$ where R$_b$ is an alkylene chain as defined above and R$_c$ is one or more aryl groups as defined above, for example, benzyl, diphenylmethyl and the like. Unless stated otherwise specifically in the specification, an aralkyl group is optionally substituted.

Aralkylamino" refers to a group of the formula —NR$_a$R$_b$ where R$_a$ is aralkyl, as defined above, and R$_b$ is H, alkyl, as defined above containing one to twelve carbon atoms, aryl as defined above, or aralkyl, as defined above. Unless stated otherwise specifically in the specification, an arylamino group is optionally substituted.

A "carbocyclic ring" is a ring wherein each ring atom is carbon. Carbocyclic rings may saturated or unsaturated, including aromatic rings. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cycloalkyl groups include, for example, cyclopropyl, cyclobutyl, cyclopentyl, cyclohexyl, cycloheptyl, and cyclooctyl. Polycyclic cycloalkyl groups include, for example, adamantyl, norbornyl, decalinyl, 7,7-dimethyl-bicyclo[2.2.1]heptanyl, and the like. Unless otherwise stated specifically in the specification, a cycloalkyl group is optionally substituted.

"Multicyclic" refers to any molecule having more than one ring. The rings may be either, fused, spirocyclic or separated by one or more atoms (e.g., linked via an acyclic linker).

"Spirocyclic" refers to a multicyclic molecule wherein two rings share a single carbon atom.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Heterocyclyl" or "heterocyclic ring" refers to a stable 3- to 18-membered aromatic (heteroaryl) or non-aromatic ring group, wherein at least one ring atom is a heteroatom selected from the group consisting of nitrogen, oxygen and sulfur, and the remaining ring atoms are selected from the group consisting of carbon nitrogen, oxygen and sulfur. Unless stated otherwise specifically in the specification, the heterocyclyl group may be a monocyclic, bicyclic, tricyclic or tetracyclic ring system, which may include fused or bridged ring systems; and the nitrogen, carbon or sulfur atoms in the heterocyclyl group may be optionally oxidized; the nitrogen atom may be optionally quaternized; and the heterocyclyl group may be partially or fully saturated. Examples of such heterocyclyl groups include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group is optionally substituted.

"Heteroaryl" refers to a 5- to 14-membered ring system group comprising one to thirteen carbon atoms, one to six heteroatoms selected from the group consisting of nitrogen, oxygen and sulfur, and at least one aromatic ring. For purposes of this invention, the heteroaryl group may be a monocyclic, bicyclic, tricyclic or tetracyclic ring system, which may include fused or bridged ring systems; and the nitrogen, carbon or sulfur atoms in the heteroaryl group may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted.

"Hydroxylalkyl" refers to an alkyl group comprising at least one hydroxyl substituent. The one or more —OH substituents may be on a primary, secondary or tertiary carbon atom. Unless stated otherwise specifically in the specification, hydroxyalkyl group is optionally substituted.

"Hydroxylalkylene" refers to an alkylene group comprising at least one hydroxyl substituent. The one or more —OH substituents may be on a primary, secondary or tertiary carbon atom. Unless stated otherwise specifically in the specification, hydroxyalkylene group is optionally substituted.

"Hydroxylalkylether" refers to an alkylether group comprising at least one hydroxyl substituent. The one or more —OH substituents may be on a primary, secondary or tertiary carbon atom. Unless stated otherwise specifically in the specification, hydroxyalkylether group is optionally substituted.

"Phosphate" refers to the $—OP(=O)(R_a)R_b$ group, wherein $R_a$ is $O^-$ or $OR_c$; and $R_b$ is $O^-$, $OR_c$, a further phosphate group (as in diphosphate and triphosphate) thiophosphate, phosphoalkyl, thiophosphoalkyl, phosphoalkylether or thiophosphoalkylether, wherein $R_c$ is a counter ion (e.g., H+, Na+ and the like).

"Phospho" refers to the divalent $—OP(=O)(R_a)O—$ group, wherein $R_a$ is $O^-$ or $OR_c$; wherein $R_c$ is a counter ion (e.g., H+, Na+ and the like).

"Phosphoalkyl" refers to the $—OP(=O)(R_a)R_b$ group, wherein $R_a$ is $O^-$ or $OR_c$; and $R_b$ is —Oalkyl, wherein $R_c$ is a counter ion (e.g., H+, Na+ and the like). Unless stated otherwise specifically in the specification, a phosphoalkyl group is optionally substituted. For example, in certain embodiments, the alkyl moiety in a phosphoalkyl group is optionally substituted with one or more of hydroxyl, amino, sulfhydryl or a phosphate, thiophosphate, phosphoalkyl, thiophosphoalkyl, phosphoalkylether or thiophosphoalkylether, which substituent is optionally substituted.

"Phosphoalkylene" refers to the divalent $—OP(=O)(R_a)R_b—$ group, wherein $R_a$ is $O^-$ or $OR_c$; and $R_b$ is —Oalkylene, wherein $R_e$ is a counter ion (e.g., H+, Na+ and the like). Unless stated otherwise specifically in the specification, a phosphoalkylene group is optionally substituted. For example, in certain embodiments, the alkylene moiety in a phosphoalkyl group is optionally substituted with one or more of hydroxyl, amino, sulfhydryl or a phosphate, thiophosphate, phosphoalkyl, thiophosphoalkyl, phosphoalkylether or thiophosphoalkylether, which substituent is optionally substituted.

"Phosphoalkylether" refers to the $—OP(=O)(R_a)R_b$ group, wherein $R_a$ is $O^-$ or $OR_c$; and $R_b$ is —Oalkylether (including polyalkylethers such as polyethyleneoxide ethers and the like), wherein $R_c$ is a counter ion (e.g., H+, Na+ and the like). Unless stated otherwise specifically in the specification, a phosphoalkylether group is optionally substituted. For example, in certain embodiments, the alkylether moiety in a phosphoalkylether group is optionally substituted with one or more of hydroxyl, amino, sulfhydryl, phosphate, phospho, thiophospho, thiophosphate, phosphoalkyl, thiophosphoalkyl, phosphoalkylether or thiophosphoalkylether, which substituents are optionally substituted.

"Phosphoramidite" refers to the $—OP(OR^a)(NR^b{}_2)$ group, wherein $R^a$ is alkyl and each $R^b$ is independently H or alkyl. Unless stated otherwise specifically in the specification, a phosphoramidite group is optionally substituted.

"Activated phosphorous" refers to any moiety comprising phosphorous which is cable of reaction with a nucleophile, for example reacting with a nucleophile at the phosphorous atom. For example, phosphoramidites and moieties comprising P-halogen bonds are included within the definition of activated phosphorous moieties. Unless stated otherwise specifically in the specification, an activated phosphorous group is optionally substituted.

"Thiophosphate" refers to the $—R_dP(=R_a)(R_b)R_c$ group, wherein $R_a$ and $R_d$ are each independently O or S; $R_b$ is $O^-$, $S^-$, $OR_e$ or $SR_e$; $R_c$ is $O^-$, $OR_e$, $S^-$, $SR_e$, a phosphate group, thiophosphate, phosphoalkyl, thiophosphoalkyl, phosphoalkylether or thiophosphoalkylether; wherein $R_e$ is a counter ion (e.g., H$^+$, Na+ and the like) and provided that: $R_a$ is S; or $R_b$ is S$^-$ or $SR_e$; or $R_c$ is S$^-$ or $SR_e$; or Rd is S, or combinations thereof.

"Thiophospho" refers to the divalent —$R_dP(=R_a)(R_b)R_c$— group, wherein $R_a$, $R_c$ and $R_d$ are each independently O or S; $R_b$ is O$^-$, S$^-$, $OR_e$ or $SR_e$; wherein $R_e$ is a counter ion (e.g., H$^+$, Na+ and the like) and provided that: $R_a$ is S; or $R_b$ is S$^-$ or $SR_e$; or $R_c$ is S; or $R_d$ is S, or combinations thereof.

"Thiophosphoalkyl" refers to the —$R_dP(=R_a)(R_b)R_c$ group, wherein $R_a$ and $R_d$ are each independently O or S, $R_b$ is O$^-$, S$^-$, $OR_e$ or $SR_e$; and $R_c$ is —Oalkyl or —Salkyl, wherein $R_e$ is a counter ion (e.g., H+, Na+ and the like) and provided that: $R_a$ is S; or $R_b$ is S$^-$ or $SR_e$; or Rc is —Salkyl; or $R_d$ is S, or combinations thereof. Unless stated otherwise specifically in the specification, a thiophosphoalkyl group is optionally substituted. For example, in certain embodiments, the alkyl moiety in a thiophosphoalkyl group is optionally substituted with one or more of hydroxyl, amino, sulfhydryl, phosphate, thiophosphate, phosphoalkyl, thiophosphoalkyl, phosphoalkylether or thiophosphoalkylether, which substituents are optionally substituted.

"Thiophosphoalkylene" refers to the divalent —$R_dP(=R_a)(R_b)R_c$— group, wherein $R_a$ and $R_d$ are each independently O or S, $R_b$ is O$^-$, S$^-$, $OR_e$ or $SR_e$; and $R_c$ is —Oalkylene or —Salkylene, wherein $R_e$ is a counter ion (e.g., H+, Na+ and the like) and provided that: $R_a$ is S; or $R_b$ is S$^-$ or $SR_e$; or Rc is —Salkylene; or $R_d$ is S, or combinations thereof. Unless stated otherwise specifically in the specification, a thiophosphoalkylene group is optionally substituted. For example, in certain embodiments, the alkylene moiety in a thiophosphoalkylene group is optionally substituted with one or more of hydroxyl, amino, sulfhydryl, phosphate, thiophosphate, phosphoalkyl, thiophosphoalkyl, phosphoalkylether or thiophosphoalkylether, which substituents are optionally substituted.

"Thiophosphoalkylether" refers to the —$R_dP(=R_a)(R_b)R_c$ group, wherein $R_a$ and $R_d$ are each independently O or S, $R_b$ is O$^-$, S$^-$, $OR_e$ or $SR_e$; and $R_c$ is —Oalkylether or -Salkylether, wherein $R_e$ is a counter ion (e.g., H+, Na+ and the like) and provided that: $R_a$ is S; or $R_b$ is S$^-$ or $SR_d$; or $R_c$ is —Salkylether; or $R_d$ is S, or combinations thereof. Unless stated otherwise specifically in the specification, a thiophosphoalkylether group is optionally substituted. For example, in certain embodiments, the alkylether moiety in a thiophosphoalkyl group is optionally substituted with one or more of hydroxyl, amino, sulfhydryl, phosphate, phospho, thiophospho, thiophosphate, phosphoalkyl, thiophosphoalkyl, phosphoalkylether or thiophosphoalkylether, which substituents are optionally substituted.

The term "substituted" used herein means any of the above groups (e.g., alkyl, alkylene, aminoalkylene, alkoxy, alkylamino, alkylcarbonyl, alkylcarbonyloxy, alkylether, polyalkylether, hydroxylpolyalkylether, aminopolyalkylether, alkylenether, polyalkylenether, hydroxylpolyalkylenether, aminopolyalkylenether, aryl, arylamino, aryloxy, arylcarbonyl, arylcarbonyloxy, aralkyl, aralkylamino, carbocyclic ring, cycloalkyl, heterocyclyl, heteroaryl, heteroarylalkyl, hydroxylalkyl, hydroxylalkylene, hydroxylalkylether, phosphoalkyl, phosphoalkylene, phosphoalkylether, phosphoramidite, activated phosphorous, thiophosphoalkyl, thiophosphoalkylene and/or thiophosphoalkylether) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions. Linkers include linear linkers, cyclic linkers and combinations thereof. In some embodiments a linker is alkylene or heteroalkylene.

For purposes of embodiments of the present invention, the term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the invention (i.e., compounds of structure (I) having a biomolecule linked thereto) are prepared, as further described herein, by contacting a biomolecule with a compound having a "M" group that enables attachment of the biomolecule to the compound via any available atom or functional group, such as an amino, hydroxy, carboxyl, or sulfhydryl group on the biomolecule.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}$ $cm^{-1}$. The biomolecules of the invention may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the invention, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Nonlimiting examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

The visually detectable biomolecules of embodiments of the invention are useful for a wide variety of biochemical and biomedical applications in which there is a need to determine the presence, location, or quantity of a particular biomolecule. In another aspect, therefore, the invention provides a method for visually detecting a biomolecule, comprising: (a) providing a biological system with a visually detectable biomolecule comprising the compound of structure (I) linked to a biomolecule; and (b) detecting the biomolecule by its visible properties. For purposes of embodiments of the invention, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Nonlimiting examples of such biological systems include cells, cell extracts, tissue samples, electrophoretic gels, assay mixtures, and hybridization reaction mixtures.

"Microparticle" refers to any of a number of small particles useful for attachment to compounds of the invention, including, but not limited to, glass beads, magnetic beads, polymeric beads, nonpolymeric beads, and the like. In certain embodiments, a microparticle comprises polystyrene, such as polystyrene beads.

Embodiments of the invention disclosed herein are also meant to encompass all compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively.

Isotopically-labeled compounds of structure (I) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. The present invention includes all solvates of the described compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

The compounds of the invention (e.g., compounds of structure (I)), or their salts, tautomers or solvates may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

"Bonding" refers to the process by which one molecule or atom associates with another atom or molecule. Bonding includes, ionic bonding, covalent bonding, chelation, association complexes, hydrogen bonding and the like. A moiety capable of bonding with an analyte molecule or solid support is moiety capable of associating with the analyte molecule or solid support by any of the above means. In one embodiments, the moiety binds with the analyte molecule or solid support by covalent bonding (i.e., the moiety is capable of forming a covalent bond with the analyte molecule or solid support).

As noted above, in one embodiment of the present invention, compounds useful as fluorescent and/or colored dyes in various analytical methods are provided. In some embodiments, the compounds have the following structure (I):

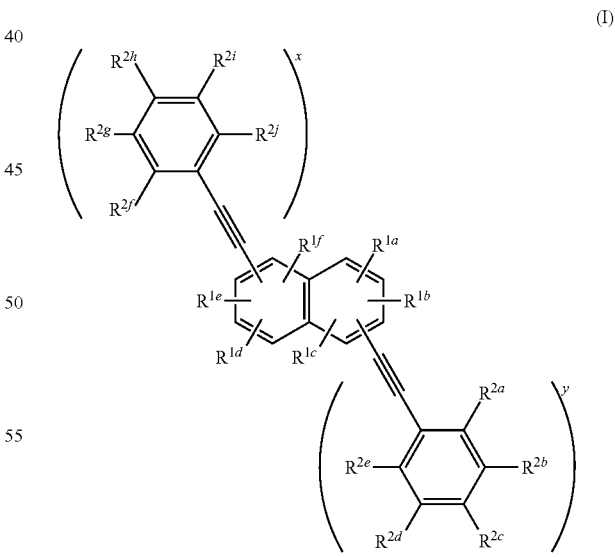

or a salt thereof, wherein:

$R^{1a}$, $R^{1b}$, $R^{1c}$, $R^{1d}$, $R^{1e}$ and $R^{1f}$ are each independently absent, H, halo, nitro, $C_1$-$C_6$ alkyl, $-SO_3^-$, $-SO_3$alkyl, $C_1$-$C_6$ alkoxy, aryl, aryloxy, $C_1$-$C_6$ alkylcarbonyl, $C_1$-$C_6$ alkylcarbonyloxy, arylcarbonyl, arylcarbonyloxy, amino, alkylamino, arylamino, aralkylamino, -$L^1$-$(R^3)_z$-$L^2$-M or -L$^1$-(R$^3$)$_z$-L$^2$—S—S—L$^2$-(R$^3$)$_z$-L$^1$—I, where I represents, independently, a further compound of structure (I); or one of R$^{1a}$, R$^{1b}$, R$^{1c}$, R$^{1d}$, R$^{1e}$ or R$^{1f}$ joins with another one of R$^{1a}$, R$^{1b}$, R$^{1c}$, R$^{1d}$, R$^{1e}$ or R$^{1f}$ to form a carbocyclic or heterocyclic ring and the remaining R$^{1a}$, R$^{1b}$, R$^{1c}$, R$^{1d}$, R$^{1e}$ and R$^{1f}$ are each independently absent, H, halo, nitro, C$_1$-C$_6$ alkyl, —OSO$_2$—, —OSO$_2$alkyl, C$_1$-C$_6$ alkoxy, aryl, aryloxy, C$_1$-C$_6$ alkylcarbonyl, C$_1$-C$_6$ alkylcarbonyloxy, arylcarbonyl, arylcarbonyloxy, amino, alkylamino, arylamino, arylalkylamino, -L$^1$-(R$^3$)$_z$-L$^2$-M or -L$^1$-(R$^3$)$_z$-L$^2$-S—S-L$^2$-(R$^3$)$_z$-L$^1$—I, where I represents, independently, a further compound of structure (I);

R$^{2a}$, R$^{2b}$, R$^{2c}$, R$^{2d}$, R$^{2e}$, R$^{2f}$, R$^{2g}$, R$^{2h}$, R$^{2i}$ and R$^{2j}$ are each independently H, halo, C$_1$-C$_6$ alkoxy, aryloxy, amino, alkylamino, arylamino, aralklyamino, heterocyclyl, -L$^1$-(R$^3$)$_z$-L$^2$-M or -L$^1$-(R$^3$)$_z$-L$^2$-S—S-L$^2$-(R$^3$)$_z$-L$^1$—I, where I represents, independently, a further compound of structure (I); or one or more of R$^{2a}$, R$^{2b}$, R$^{2c}$, R$^{2d}$, R$^{2e}$, R$^{2f}$, R$^{2g}$, R$^{2h}$, R$^{2i}$ or R$^{2j}$ join with another one or more (e.g., one or two) of R$^{2a}$, R$^{2b}$, R$^{2c}$, R$^{2d}$, R$^{2e}$, R$^{2f}$, R$^{2g}$, R$^{2h}$, R$^{2i}$ or R$^{2j}$ on the same ring to form a mono or fused bicyclic carbocyclic or heterocyclic ring and the remaining R$^{2a}$, R$^{2b}$, R$^{2c}$, R$^{2d}$, R$^{2e}$, R$^{2f}$, R$^{2g}$, R$^{2h}$, R$^{2i}$ and R$^{2j}$ are each independently H, halo, C$_1$-C$_6$ alkoxy, aryloxy, amino, alkylamino, arylamino, aralklyamino, heterocyclyl, -L$^1$-(R$^3$)$_z$-L$^2$-M or -L$^1$-(R$^3$)$_z$-L$^2$-S—S-L$^2$-(R$^3$)$_z$-L$^1$—I, where I represents, independently, a further compound of structure (I);

R$^3$ is, at each occurrence, independently a mono or bivalent functional group selected from the group consisting of polyalkyether, polyalkylenether, hydroxylalkoxy, hydroxylalkyl, hydroxylalkylene, aminoalkylene, aminoalkoxy, hydroxylpolyalkyether, hydroxylpolyalkylenether, aminopolyalkyether, aminopolyalkylenether, phosphate, thiophosphate, phospho, thiophospho, phosphoalkyl, phosphoalkylene, phosphoalkylether, thiophosphoalkyl, thiophosphoalkylene, thiophosphoalkylether, phosphoramidite and activated phosphorous;

M is absent, H or a moiety capable of bonding with an analyte molecule or a solid support; or M is an analyte molecule or solid support;

L$^1$ and L$^2$ are, at each occurrence, independently an optional linker;

x and y are each independently an integer from 0 to 4, and the sum of x and y is 2 or greater;

z is an integer from 1 to 10; and provided at least one of R$^{1a}$, R$^{1b}$, R$^{1c}$, R$^{1d}$, R$^{1e}$, R$^{1f}$, R$^{2a}$, R$^{2b}$, R$^{2c}$, R$^{2d}$, R$^{2e}$, R$^{2f}$, R$^{2g}$, R$^{2h}$, R$^{2i}$ or R$^{2j}$ is -L$^1$-(R$^3$)$_z$-L$^2$-M or -L$^1$-(R$^3$)$_z$-L$^2$-S—S-L$^2$-(R$^3$)$_z$-L$^1$—I, where I represents, independently, a further compound of structure (I).

In some embodiments, at least one of R$^{1a}$, R$^{1b}$, R$^{1c}$, R$^{1d}$, R$^{1e}$, R$^{1f}$, R$^{2a}$, R$^{2b}$, R$^{2c}$, R$^{2d}$, R$^{2e}$, R$^{2f}$, R$^{2g}$, R$^{2h}$, R$^{2i}$ or R$^{2j}$ is -L$^1$-(R$^3$)$_z$-L$^2$-M. In other embodiments, at least one of R$^{1a}$, R$^{1b}$, R$^{1c}$, R$^{1d}$, R$^{1e}$ or R$^{1f}$ is -L$^1$-(R$^3$)$_z$-L$^2$-M. In still more embodiments, at least one of R$^{2a}$, R$^{2b}$, R$^{2c}$, R$^{2d}$, R$^{2e}$, R$^{2f}$, R$^{2g}$, R$^{2h}$, R$^{2i}$ or R$^{2j}$ is -L$^1$-(R$^3$)$_z$-L$^2$-M.

In certain embodiments, the compound of structure (I) comprises two ethynylphenyl moieties, and the sum of x and y is 2. In some of these embodiments x is 0 and y is 2

In some more specific embodiments, the compound has the following structure (Ia):

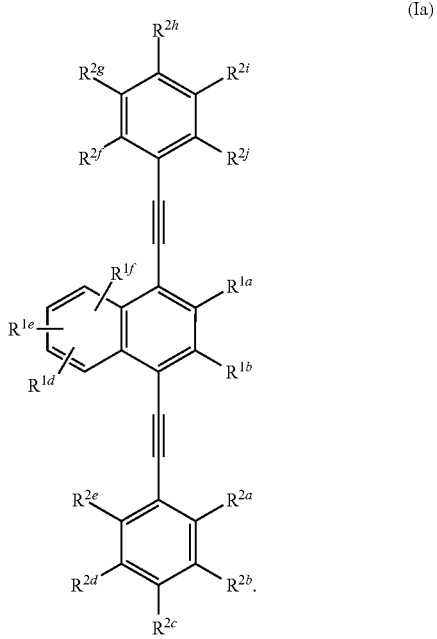

(Ia)

In other more specific embodiments, the compound has the following structure (Ib):

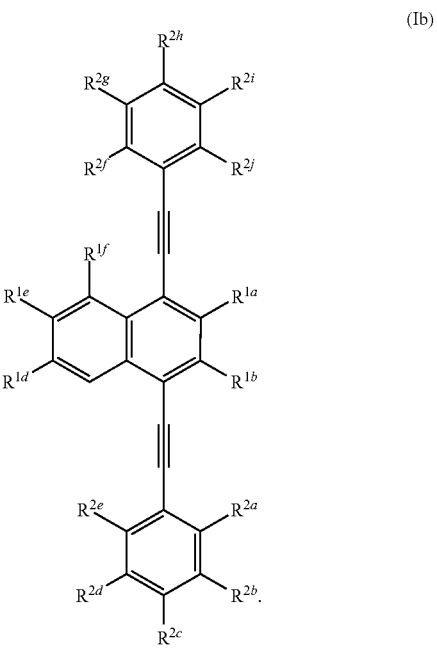

(Ib)

In some embodiments, R$^{1a}$ is -L$^1$-(R$^3$)$_z$-L$^2$-M. In other embodiments, one of R$^{1d}$, R$^{1e}$ or R$^{1f}$ is -L$^1$-(R$^3$)$_z$-L$^2$-M. In still different embodiments, one of R$^{2a}$, R$^{2b}$, R$^{2c}$, R$^{2d}$, R$^{2e}$, R$^{2f}$, R$^{2g}$, R$^{2h}$, R$^{2i}$ or R$^{2j}$ is -L$^1$-(R$^3$)$_z$-L$^2$-M. In yet other embodiments, two of R$^{2a}$, R$^{2b}$, R$^{2c}$, R$^{2d}$, R$^{2e}$, R$^{2f}$, R$^{2g}$, R$^{2h}$, R$^{2i}$ or R$^{2j}$ are -L$^1$-(R$^3$)$_z$-L$^2$-M.

In some more embodiments, $R^{1a}$ and $R^{1b}$ are both -$L^1$-$(R^3)_z$-$L^2$-M. In other embodiments, one of $R^{1a}$ or $R^{1b}$ is -$L^1$-$(R^3)_z$-$L^2$-M and one of $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$ is -$L^1$-$(R^3)_z$-$L^2$-M. In some other embodiments, one of $R^{1a}$ or $R^{1b}$ is -$L^1$-$(R^3)_z$-$L^2$-M and one of $R^{1d}$, $R^{1e}$ or $R^{1f}$ is -$L^1$-$(R^3)_z$-$L^2$-M.

In some other embodiments, at least one of $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$ is amino, alkylamino, arylamino, aralklyamino or heterocyclyl. For example, in certain embodiments $R^{2c}$ or $R^{2h}$, or both, is amino, alkylamino, arylamino, aralklyamino or heterocyclyl. In some of these embodiments, alkylamino is dimethylamino, diethylamino, diisopropylamino or ethylisopropylamino. In other of these embodiments, arylamino is diphenylamino. In still more of these embodiments, heterocyclyl is N-pyrrolidinyl or N-pyrrolyl.

In some embodiments, $R^{2a}$, $R^{2b}$, $R^{2c}$, $R^{2d}$, $R^{2e}$, $R^{2f}$, $R^{2g}$, $R^{2h}$, $R^{2i}$ and $R^{2j}$ are each independently H, halo, $C_1$-$C_6$ alkoxy, aryloxy, amino, alkylamino, arylamino, aralklyamino, heterocyclyl, -$L^1$-$(R^3)_z$-$L^2$-M or -$L^1$-$(R^3)_z$-$L^2$-S—S-$L^2$-$(R^3)_z$-$L^1$—I, where I represents, independently, a further compound of structure (I).

In other embodiments, one or more of $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$ join with another one or more (e.g., one or two) of $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$ on the same ring to form a mono or fused bicyclic carbocyclic or heterocyclic ring and the remaining $R^{2a}$, $R^{2b}$, $R^{2c}$, $R^{2d}$, $R^{2e}$, $R^{2f}$, $R^{2g}$, $R^{2h}$, $R^{2i}$ and $R^{2j}$ are each independently H, halo, $C_1$-$C_6$ alkoxy, aryloxy, amino, alkylamino, arylamino, aralklyamino, heterocyclyl, -$L^1$-$(R^3)_z$-$L^2$-M or -$L^1$-$(R^3)_z$-$L^2$-S—S-$L^2$-$(R^3)_z$-$L^1$—I, where I represents, independently, a further compound of structure (I). For example, in some embodiments, the compound has one of the following structures:

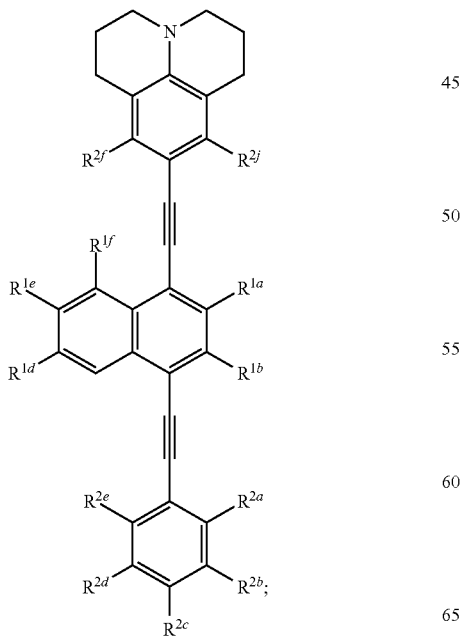

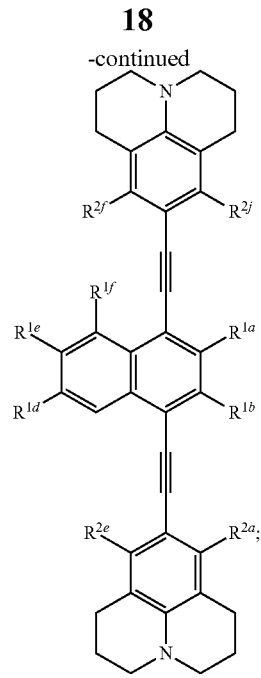

-continued

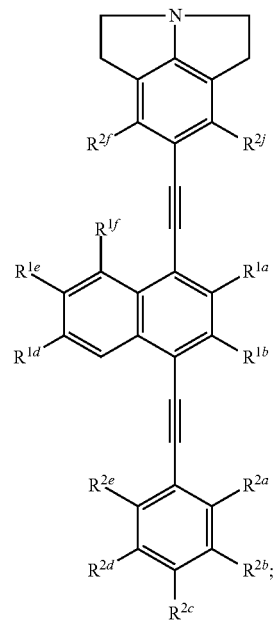

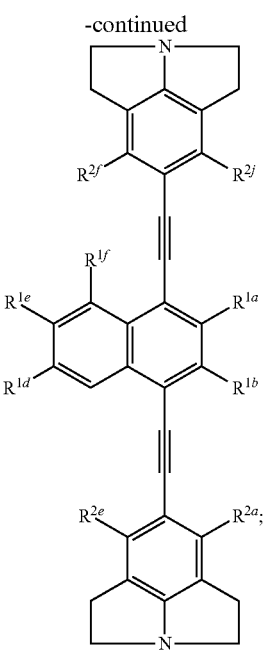
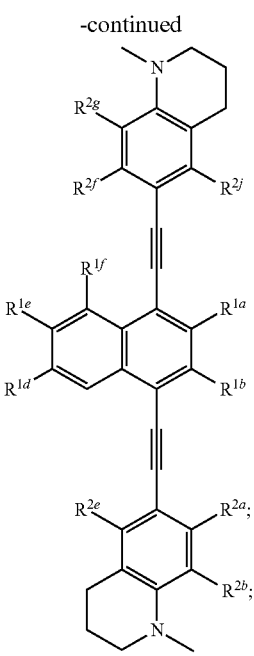
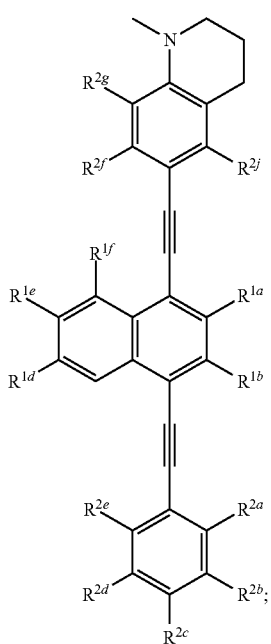
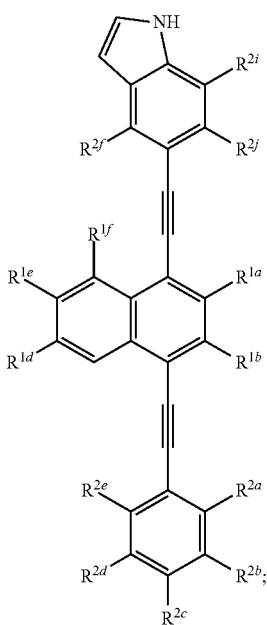

21
-continued
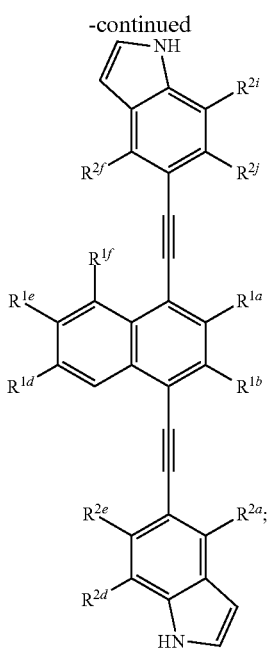
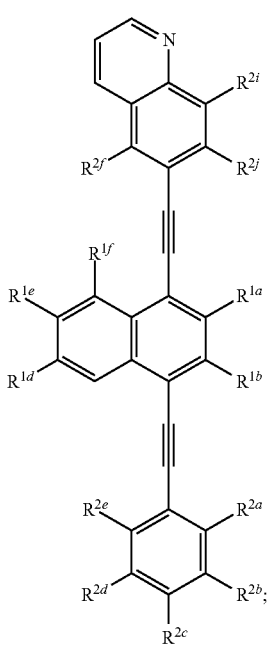
22
-continued
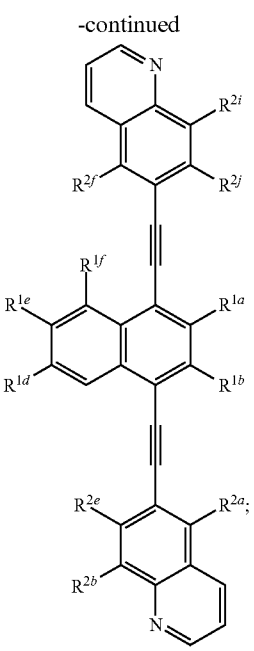
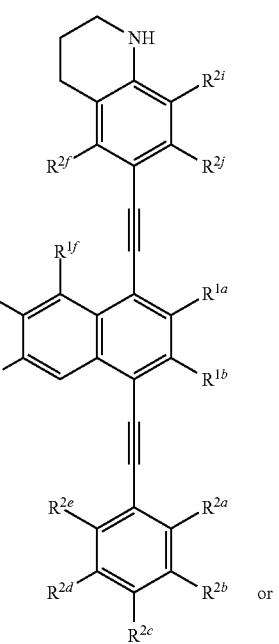 or

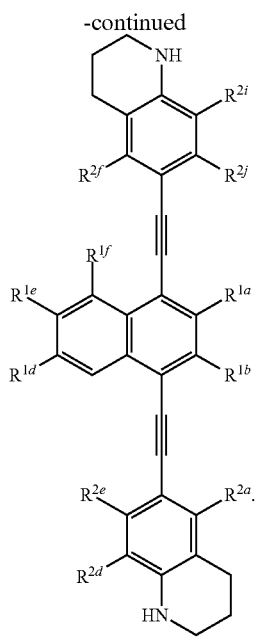

In any of the foregoing embodiments, at least one of $R^{2a}$, $R^{2b}$, $R^{2d}$, $R^{2e}$, $R^{2f}$, $R^{2g}$, $R^{2i}$ or $R^{2j}$ is halo, alkoxy or aryloxy. For example, in some embodiments at least one of $R^{2a}$, $R^{2b}$, $R^{2d}$, $R^{2e}$, $R^{2f}$, $R^{2g}$, $R^{2i}$ or $R^{2j}$ is halo. In other embodiments at least one of $R^{2a}$, $R^{2b}$, $R^{2d}$, $R^{2e}$, $R^{2f}$, $R^{2g}$, $R^{2i}$ or $R^{2j}$ is alkoxy. In still other embodiments, at least one of $R^{2a}$, $R^{2b}$, $R^{2d}$, $R^{2e}$, $R^{2f}$, $R^{2g}$, $R^{2i}$ or $R^{2j}$ is aryloxy.

In other of any of the foregoing embodiments, at least one of $R^{2a}$, $R^{2b}$, $R^{2d}$, $R^{2e}$, $R^{2f}$, $R^{2g}$, $R^{2i}$ or $R^{2j}$ is H. For example, in some embodiments each of $R^{2a}$, $R^{2b}$, $R^{2d}$, $R^{2e}$, $R^{2f}$, $R^{2g}$, $R^{2i}$ and $R^{2j}$ is H.

In some other of any of the foregoing embodiments, $R^{1a}$, $R^{1b}$, $R^{1c}$, $R^{1d}$, $R^{1e}$ and $R^{1f}$ are each independently absent, H, halo, nitro, $C_1$-$C_6$ alkyl, —$SO_3^-$, —$SO_3$alkyl, $C_1$-$C_6$ alkoxy, aryl, aryloxy, $C_1$-$C_6$ alkylcarbonyl, $C_1$-$C_6$ alkylcarbonyloxy, arylcarbonyl, arylcarbonyloxy, amino, alkylamino, arylamino, aralklyamino, -$L^1$-$(R^3)_z$-$L^2$-M or -$L^1$-$(R^3)_z$-$L^2$-S—S-$L^2$-$(R^3)_z$-$L^1$—I, where I represents, independently, a further compound of structure (I).

For example, in some embodiments at least one of $R^{1a}$, $R^{1b}$, $R^{1c}$, $R^{1d}$, $R^{1e}$ or $R^{1f}$ is $C_1$-$C_6$ alkoxy, aryloxy or $C_1$-$C_6$ alkylcarbonyloxy. In some of these embodiments, $C_1$-$C_6$ alkoxy is methoxy.

In other of the foregoing embodiments, at least one of $R^{1a}$, $R^{1b}$, $R^{1c}$, $R^{1d}$, $R^{1e}$ or $R^{1f}$ is amino, alkylamino, arylamino or aralklyamino. In some of these embodiments, alkylamino is dimethylamino.

In other embodiments, at least one of $R^{1a}$, $R^{1b}$, $R^{1c}$, $R^{1d}$, $R^{1e}$ or $R^{1f}$ is halo or nitro.

In yet other embodiments, at least one of $R^{1a}$, $R^{1b}$, $R^{1c}$, $R^{1d}$, $R^{1e}$ or $R^{1f}$ is —$SO_3^-$ or —$SO_3$alkyl.

In some more embodiments, at least one of $R^{1a}$, $R^{1b}$, $R^{1c}$, $R^{1d}$, $R^{1e}$ or $R^{1f}$ is $C_1$-$C_6$ alkyl or aryl. In some of these embodiments, $C_1$-$C_6$ alkyl is methyl or ethyl.

In other of any of the foregoing embodiments, at least one of $R^{1a}$, $R^{1b}$, $R^{1c}$, $R^{1d}$, $R^{1e}$ or is alkylcarbonyl or arylcarbonyl.

In more embodiments of any of the foregoing compounds of structure (I), one of $R^{1a}$, $R^{1b}$, $R^{1c}$, $R^{1d}$, $R^{1e}$ or $R^{1f}$ joins with another one of $R^{1a}$, $R^{1b}$, $R^{1c}$, $R^{1d}$, $R^{1e}$ or $R^{1f}$ to form a carbocyclic or heterocyclic ring and the remaining $R^{1a}$, $R^{1b}$, $R^{1c}$, $R^{1d}$, $R^{1e}$ and $R^{1f}$ are each independently absent, H, halo, nitro, $C_1$-$C_6$ alkyl, —$OSO_2^-$, —$OSO_2$alkyl, $C_1$-$C_6$ alkoxy, aryl, aryloxy, $C_1$-$C_6$ alkylcarbonyl, $C_1$-$C_6$ alkylcarbonyloxy, arylcarbonyl, arylcarbonyloxy, amino, alkylamino, arylamino, aralklyamino, -$L^1$-$(R^3)_z$-$L^2$-M or -$L^1$-$(R^3)_z$-$L^2$-S—S-$L^2$-$(R^3)_z$-$L^1$—I, where I represents, independently, a further compound of structure (I).

In other of any of the foregoing embodiments, the compound has one of the following structures:

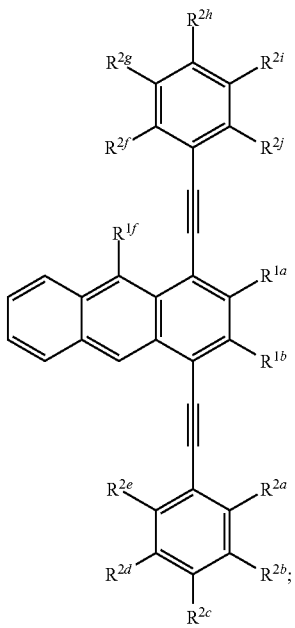

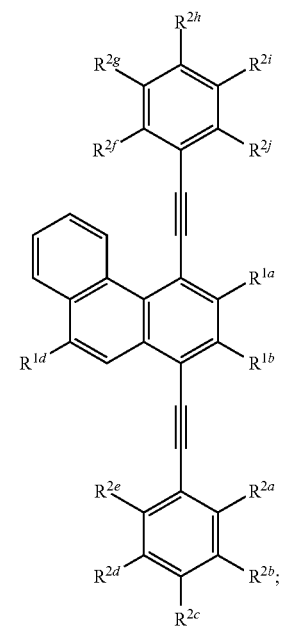

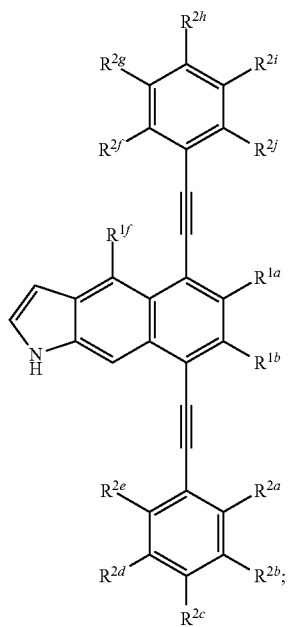

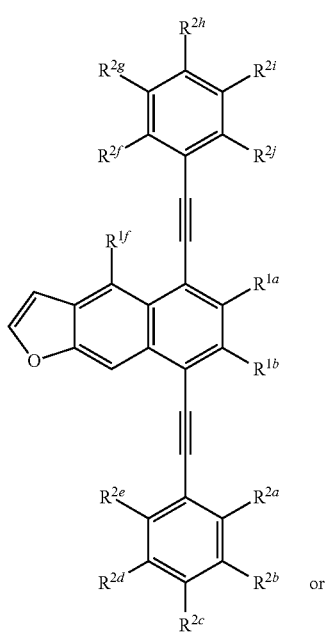 or

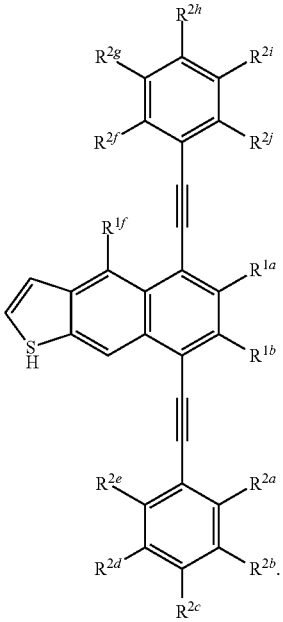

In some embodiments, $L^1$ is present. For example, in certain embodiments $L^1$ is $C_1$-$C_6$ alkylene. In certain other embodiments $L^1$ is $C_1$-$C_6$ heteroalkylene.

In some embodiments, $L^2$ is present. For example, in certain embodiments $L^2$ is $C_1$-$C_6$ alkylene. In certain other embodiments $L^2$ is $C_1$-$C_6$ heteroalkylene. In other embodiments, $L^2$ comprises a cyclic linking moiety.

In certain embodiments of any of the foregoing compounds, $R^3$ is selected from the group consisting of polyalkylether, phosphate, phospho and phosphoalkyl. For example, in some embodiments $R^3$ is selected from the group consisting of:

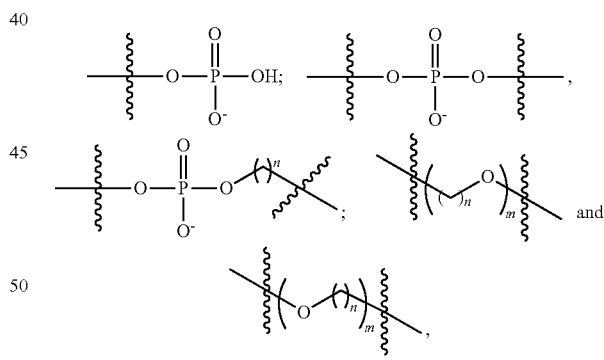

wherein n is an integer from 1 to 6 and m is an integer from 2 to 10.

In still other embodiments, $-(R^3)_z-L^2-M$ has one of the following structures:

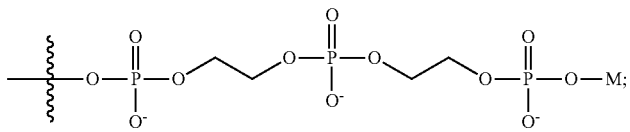

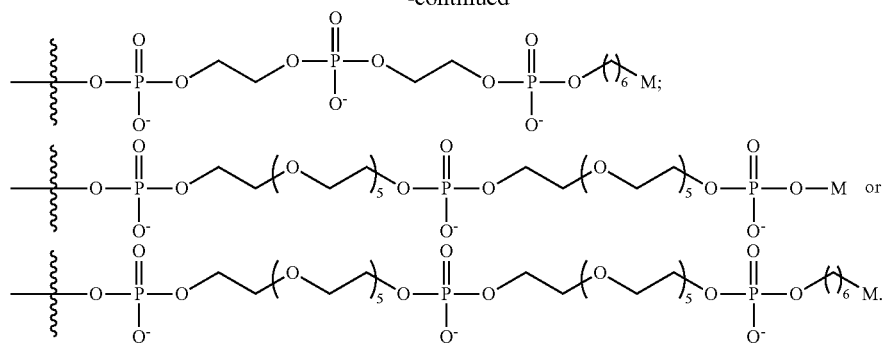

In some different embodiments, $R^3$ is phosphoramidite and M is absent.

In other embodiments, M is absent or H.

In still other embodiments, M is a moiety capable of bonding with an analyte molecule or a solid support. In certain embodiments, M provides a means of connecting the compound of structure (I) to an analyte molecule or a solid support (e.g., by a covalent bond). For example, in some embodiments M is a reactive group capable of forming a covalent bond with an analyte molecule or a solid support. In this regard the type of M group and connectivity of the M group to the remainder of the compound of structure (I) is not limited. In certain embodiments, the M is a moiety which is not susceptible to hydrolysis under aqueous conditions, but is sufficiently reactive to form a bond with a corresponding group on an analyte molecule or solid support (e.g., an amine).

Certain embodiments of compounds of structure (I) comprises M groups commonly employed in the field of bioconjugation. For example in some embodiments, M is a nucleophilic reactive group, an electrophilic reactive group or a cycloaddition reactive group. In some more specific embodiments, M is sulfhydryl, disulfide, activated ester, isothiocyanate, azide, alkyne, alkene, diene, dienophile, acid halide, sulfonyl halide, phosphine, α-haloamide, biotin, amino or a maleimide. In some embodiments, the activated ester is an N-succinimide ester, imidoester or polyflourophenyl ester. In other embodiments, the alkyne is an alkyl azide or acyl azide.

Exemplary M moieties are provided in Table I below.

TABLE 1

Exemplary M Moieties

| Structure | Class |
|---|---|
| —SH | Sulfhydryl |
| —N=C=S | Isothiocyanate |
| (imidoester structure with OMe, NH$_2^+$Cl$^-$) | Imidoester |

TABLE 1-continued

Exemplary M Moieties

| Structure | Class |
|---|---|
| (acyl azide structure) | Acyl Azide |
| (tetrafluorophenyl ester) | Activated Ester |
| (sulfonated nitrophenyl ester) | Activated Ester |
| (maleimide-thiol linked sulfonated nitrophenyl ester) | Activated Ester |
| (NHS ester) | Activated Ester |

TABLE 1-continued

Exemplary M Moieties

| Structure | Class |
|---|---|
| (succinimidyl ester with SO₃⁻) | Activated Ester |
| —S(O)₂—X; X = halo | Sulfonyl halide |
| (maleimide) | Maleimide |
| (SMCC-type maleimide with cyclohexyl linker) | Maleimide |
| —N(H)—C(O)—CH₂—X; X = halo | α-haloimide |
| (pyridyl disulfide) | Disulfide |
| (methyl 4-acyl-2-(diphenylphosphino)benzoate) | Phosphine |
| —N₃ | Azide |
| —C≡CH | Alkyne |
| (biotin) | Biotin |
| (1,3-diene) | Diene |
| (alkyne) | Alkene/dienophile |
| —CH=CH—EWG | Alkene/dienophile |
| —NH₂ | Amino |

EWG = eletron withdrawing group

In some embodiments, it is advantageous to employ a compound of structure (I) wherein M is —SH since —SH can be readily conjugated to many analyte molecules and/or solid supports (e.g., by formation of a disulfide bond with a free sulfhydryl on the analyte molecule or solid support). However, for purposes of long term stability of the compounds of structure (I), it may be desirous to store the compound in the form of a disulfide dimer. Accordingly, some embodiments provide such disulfide dimers. For example, in some embodiments at least one of $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$ is -L$^1$-(R$^3$)$_z$-L$^2$-S—S-L$^2$-(R$^3$)$_z$-L$^1$—I, where I represents, independently, a further compound of structure (I).

The dimer may be formed between any one of $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$, $R^{2f}$, $R^{2g}$, $R^{2h}$, $R^{2i}$ Or $R^{2j}$ and another one of $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$. For ease of illustration, but not limitation, an exemplary dimer, wherein the dimer is formed between two $R^{1a}$ groups is illustrated below (I'):

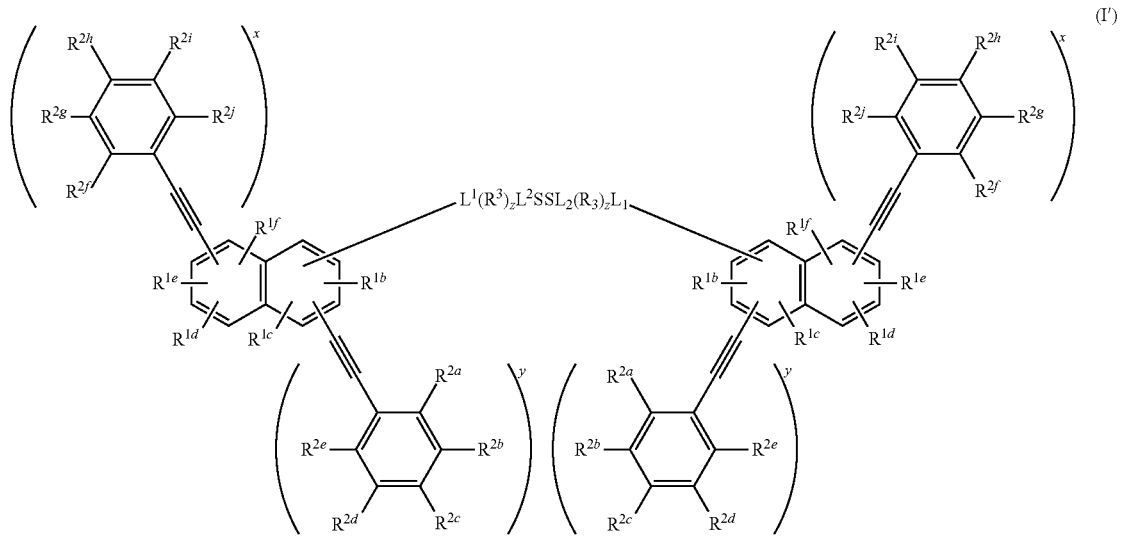

wherein $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^3$, $L^1$, $L^2$, x, y and z are each independently as defined for any of the foregoing embodiments.

The dimers are also illustrated as follows (I'):

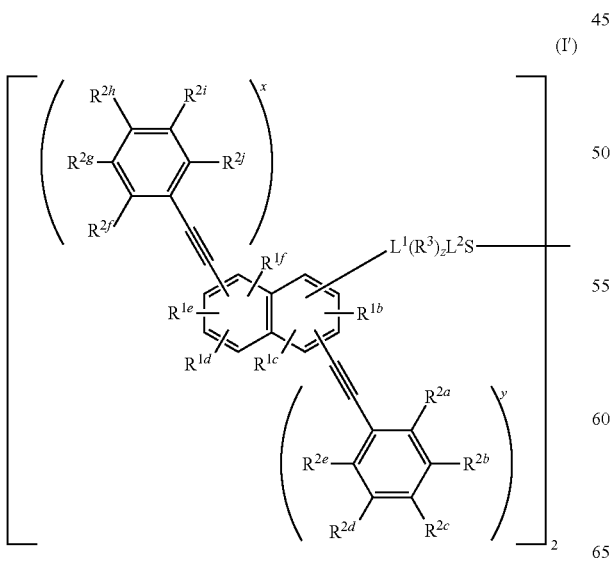

In various embodiments, the dimers have the following structure (Ia'):
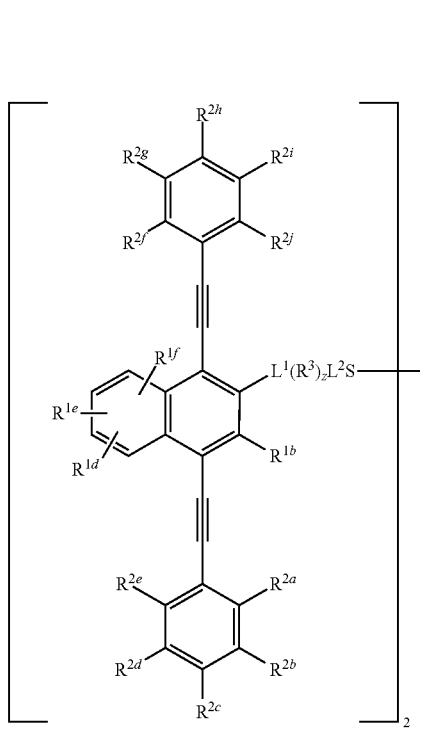
In other embodiments, the dimers have the following structure (Ib'):
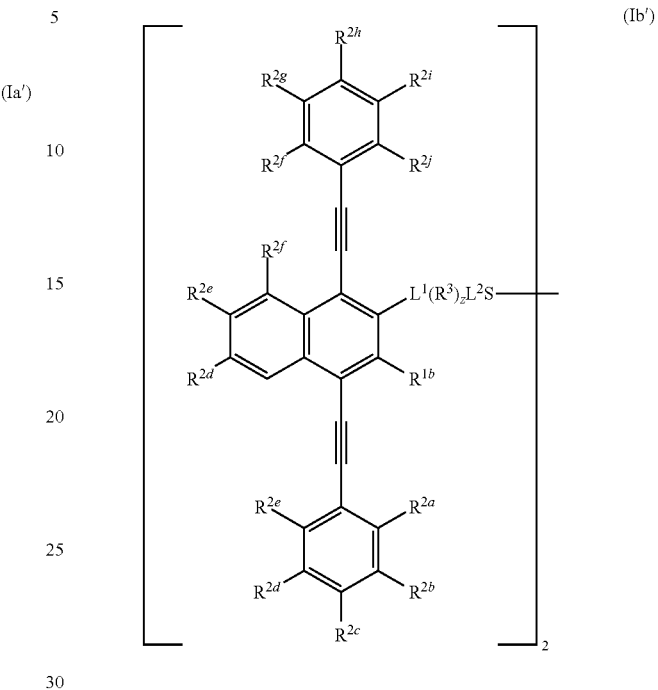
The disulfide linker between the two compounds of structure (I), i.e., -$L^1(R^3)_z$-$L^2$-S—S-$L^2$-$(R^3)_z$-$L^1$-, can have various structures. In some embodiments, -$L^1(R^3)_z$-$L^2$-S—S-$L^2$-$(R^3)_z$-$L^1$- has one of the following structures:
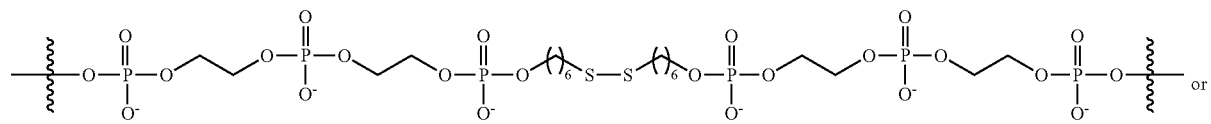 or
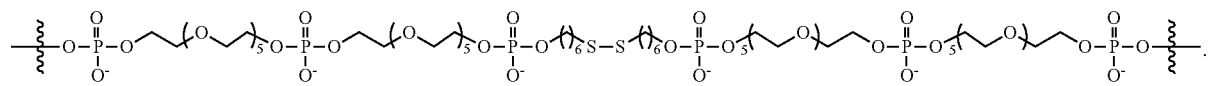

For example, in some embodiments the analyte molecule is a biomolecule. In some embodiments, the biomolecule is a nucleic acid, amino acid or a polymer thereof. In other embodiments the biomolecule is a nucleic acid, peptide, carbohydrate, lipid, enzyme, receptor, receptor ligand, antibody, glycoprotein, aptamer, antigen or prion.

In different embodiments, the analyte molecule is a drug, vitamin or small molecule.

The structure of the compound of structure (I) is typically selected to optimize the excitation and or emission wavelengths. Accordingly, in various embodiments the compound of structure (I) has a maximum excitation wavelength ranging from about 390 nm to about 430 nm, for example from about 400 nm to about 420 nm. In other embodiments, the compound of structure (I) has a maximum emission wavelength ranging from about 510 nm to about 550 nm, for example, from about 520 to about 540 nm. For example, in certain embodiment the dyes have a maximum excitation wavelength at about 410 nm and a maximum emission wavelength at about 533 nm.

In some more specific embodiments, the compound of structure (I) has one of the following structures:

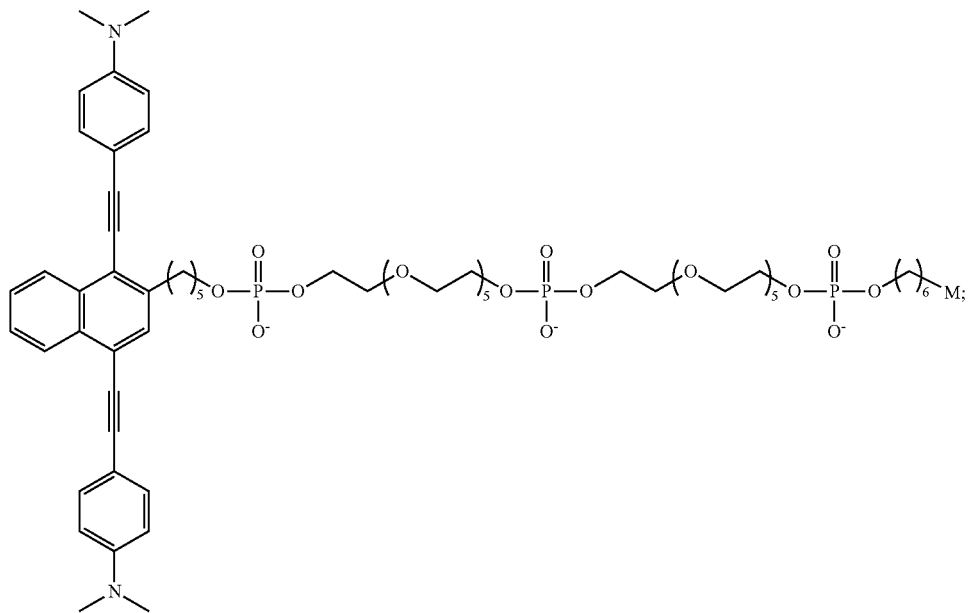

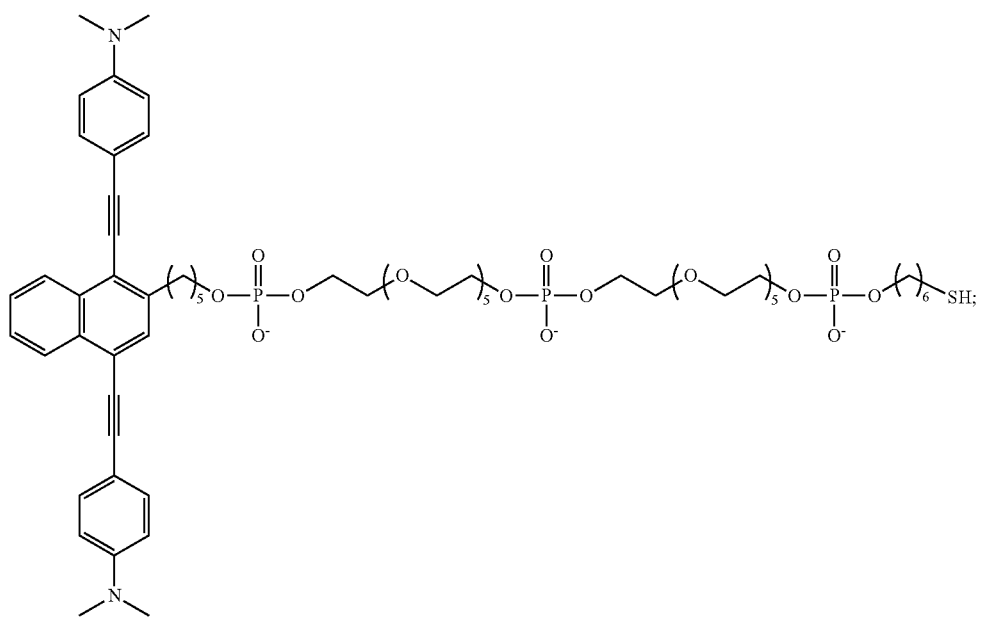

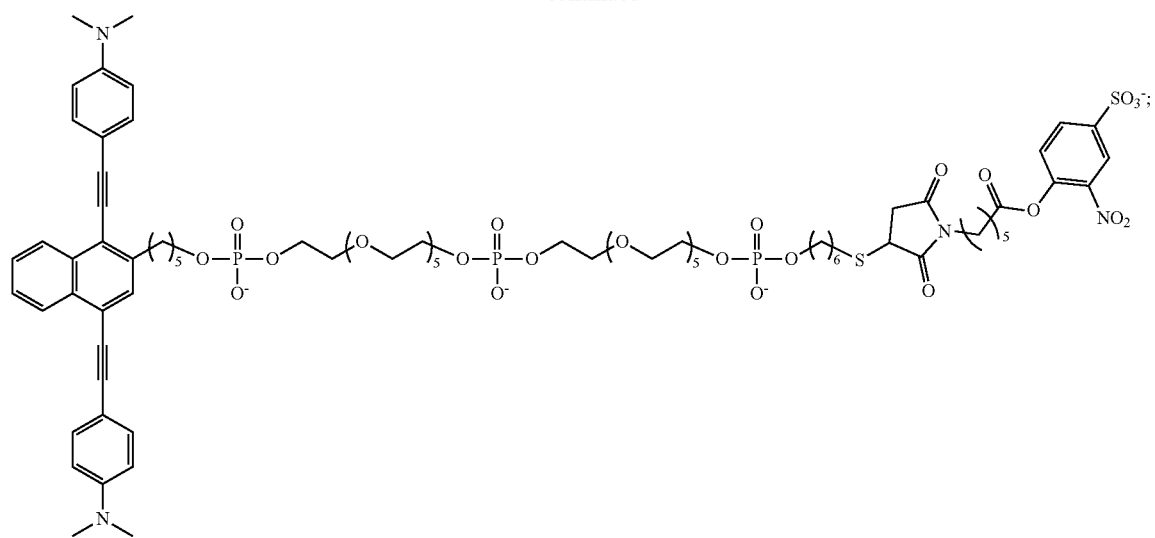
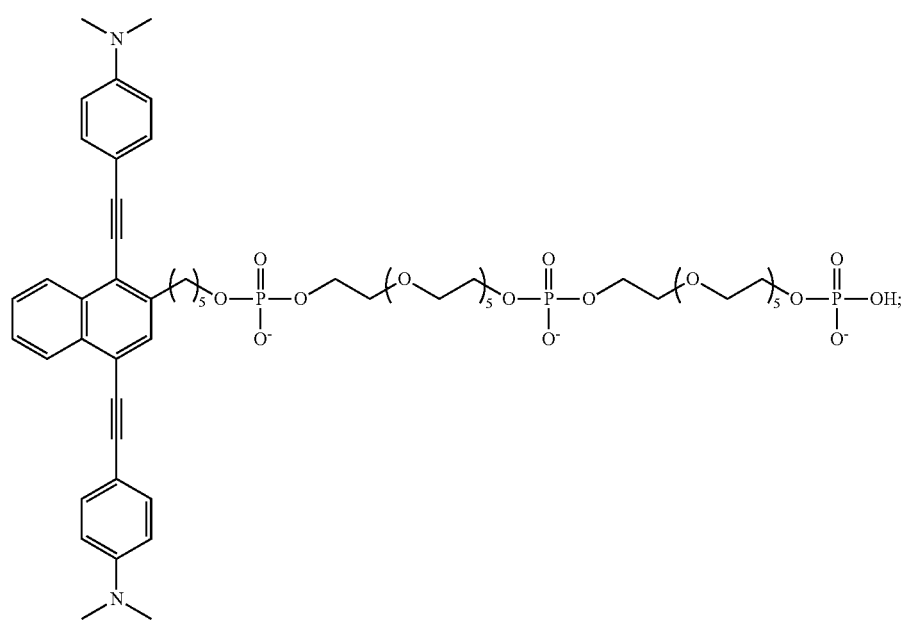

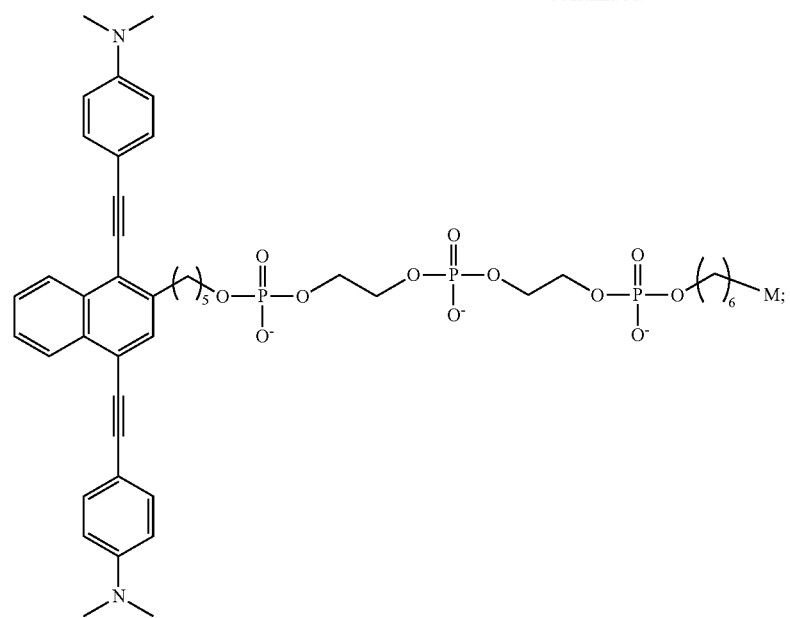
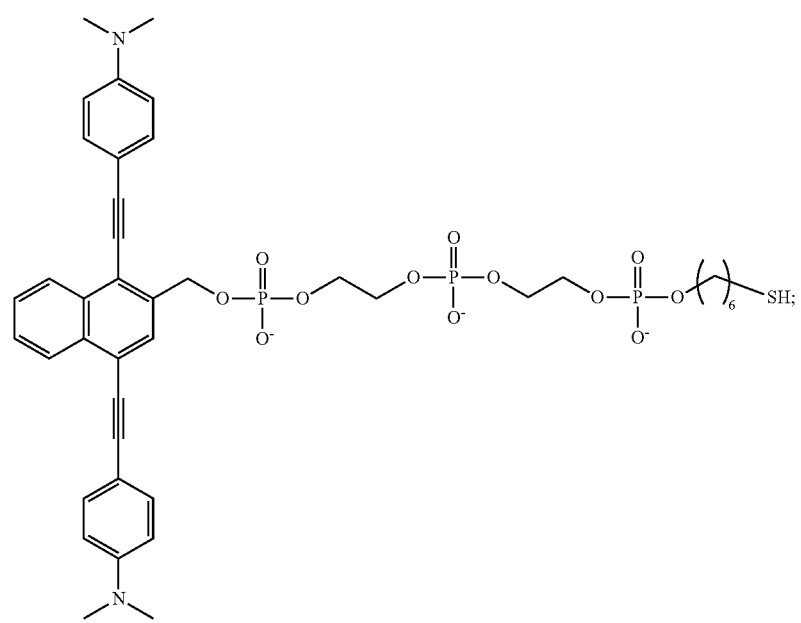

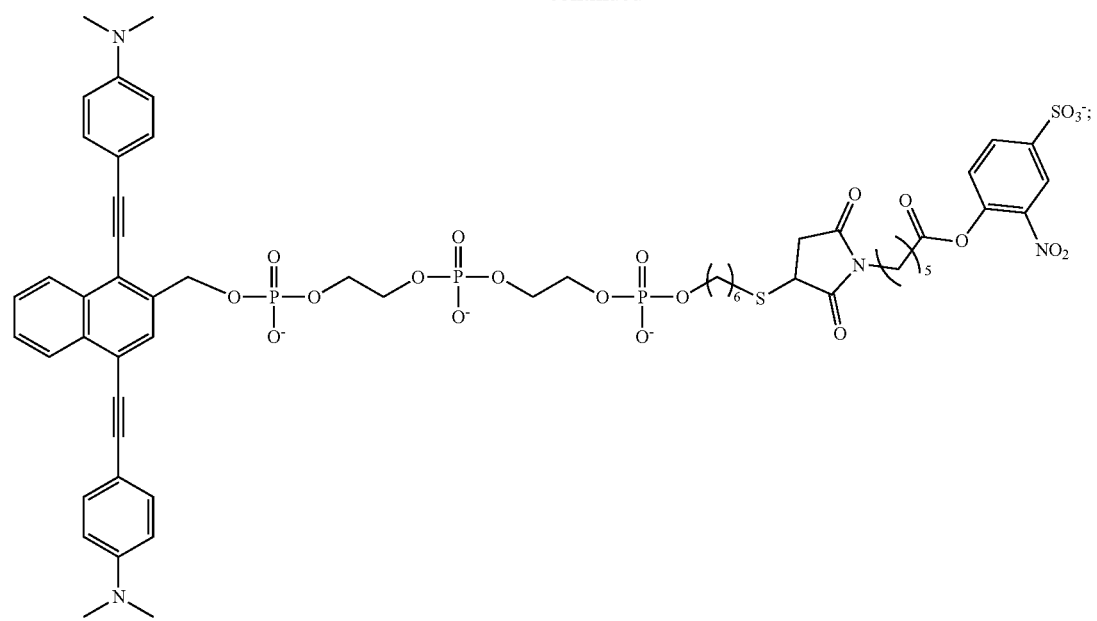
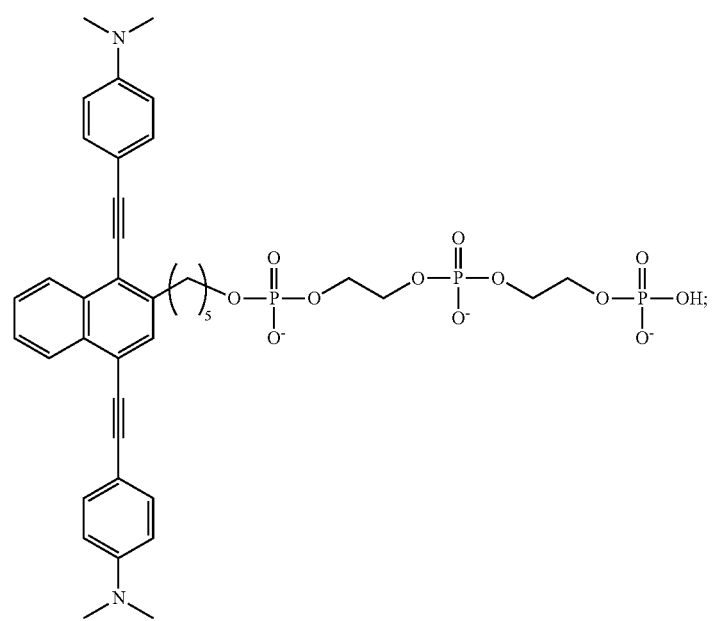

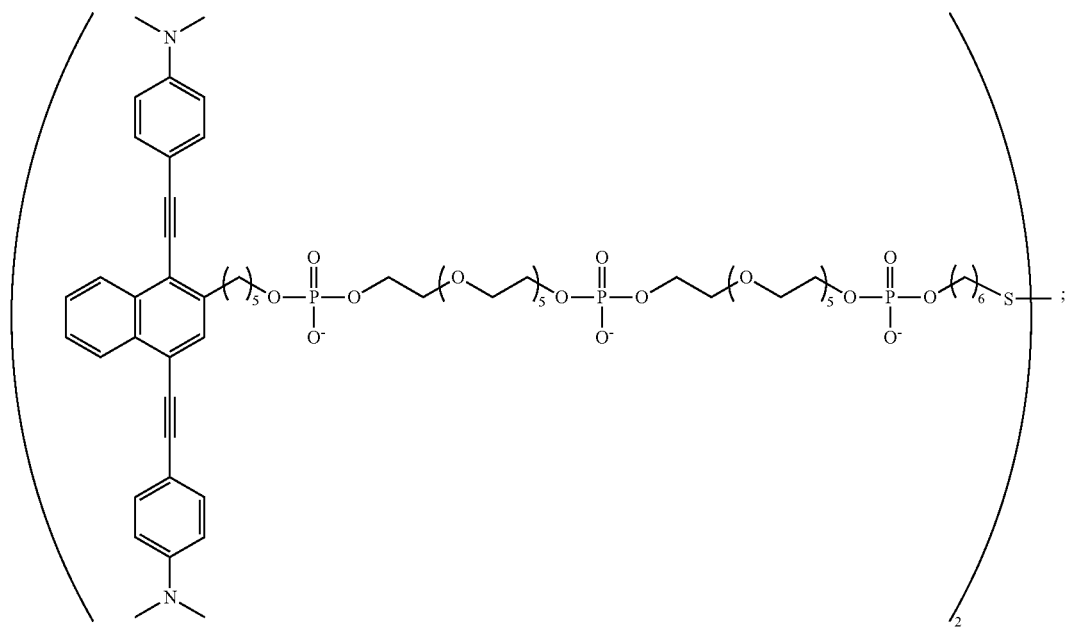
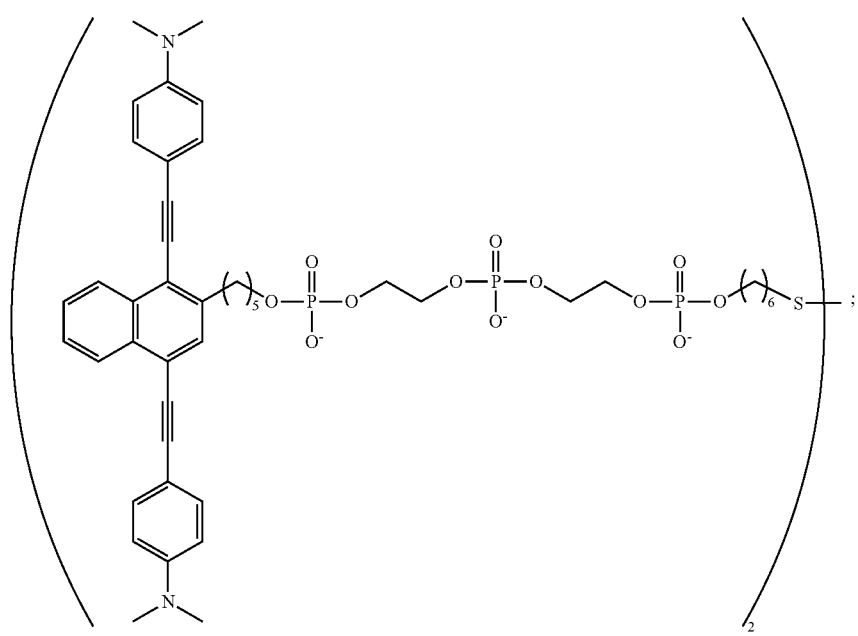

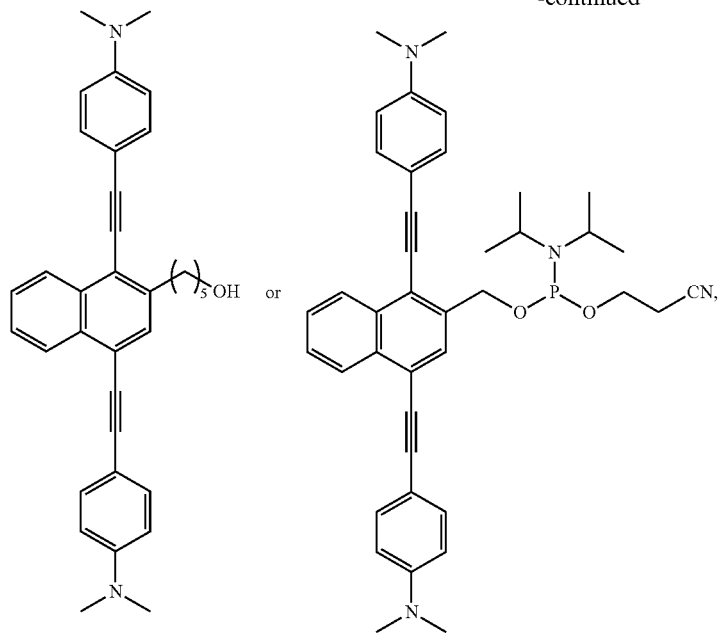

or a salt thereof, where M is a moiety capable of bonding with an analyte molecule or a solid support; or M is an analyte molecule or solid support, such as a microparticle, covalently linked via an optional linker. In some of the foregoing embodiments, M is —SH.

Compositions comprising any of the disclosed compounds and one or more biomolecules are provided in various other embodiments. In some embodiments, use of such compositions in analytical methods for detection of the one or more biomolecules is also provided as described in more detail below.

It is understood that any embodiment of the compounds of structure (I), as set forth above, and any specific choice set forth herein for a $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^3$, $L^1$, $L^2$, M, x, y or z variable in the compounds of structure (I), as set forth above, may be independently combined with other embodiments and/or variables of the compounds of structure (I) to form embodiments of the inventions not specifically set forth above. In addition, in the event that a list of choices is listed for any particular R, L, M, x, y or z group in a particular embodiment and/or claim, it is understood that each individual choice may be deleted from the particular embodiment and/or claim and that the remaining list of choices will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R″ (where R″ is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention (e.g., compounds of structure (I)) which exist in free base or acid form can be converted to their salts by treatment with the appropriate inorganic or organic base or acid by methods known to one skilled in the art. Salts of the compounds of the invention can be converted to their free base or acid form by standard techniques.

The following Reaction Scheme illustrates exemplary methods of making compounds of this invention, i.e., compound of structure (I):

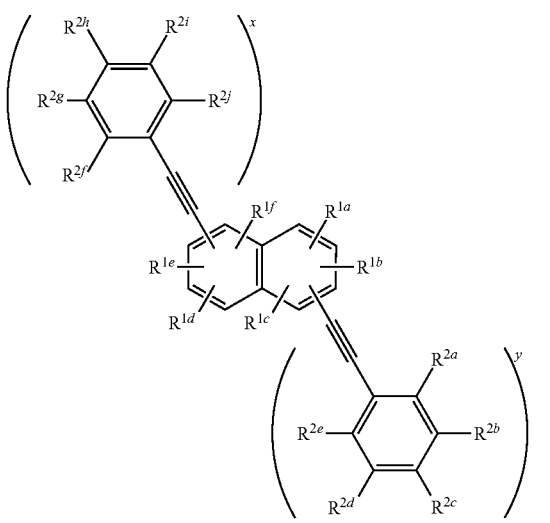

(I)

or a salt thereof, wherein $R^{1a}$, $R^{1b}$, $R^{1c}$, $R^{1d}$, $R^{1e}$, $R^{1f}$, $R^{2a}$, $R^{2b}$, $R^{2c}$, $R^{2d}$, $R^{2e}$, $R^{2f}$, $R^{2g}$, $R^{2h}R^{2i}$, $R^{2j}$, x and y are as defined herein.

It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Reaction Scheme I

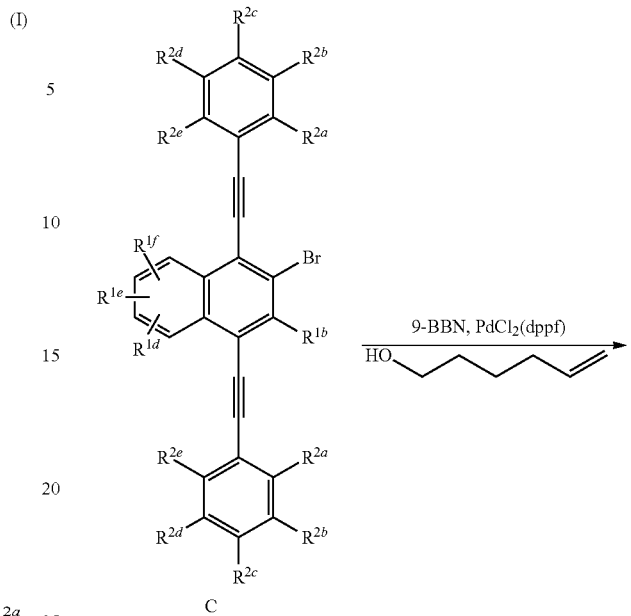

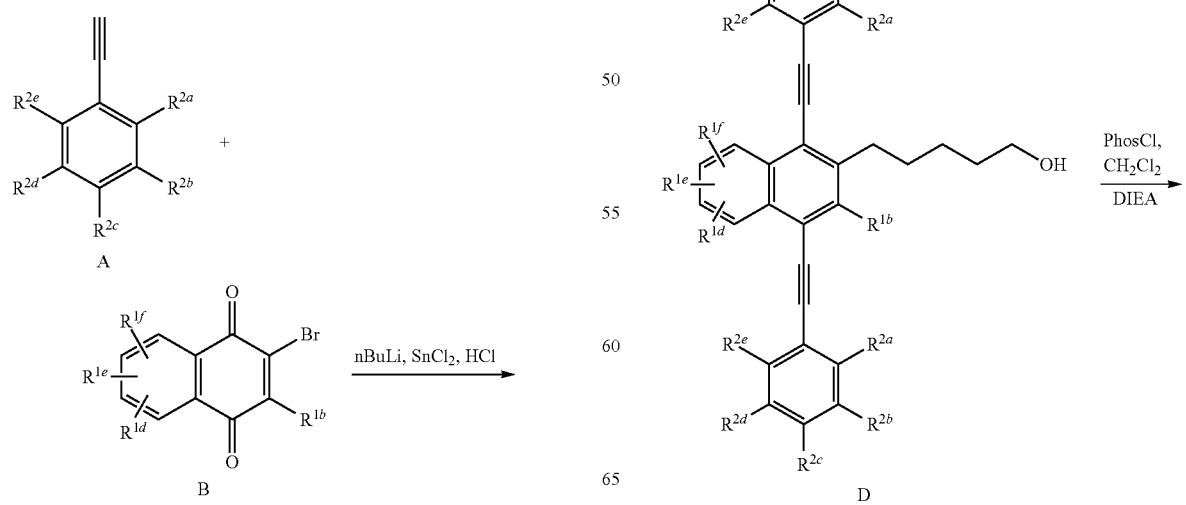

-continued

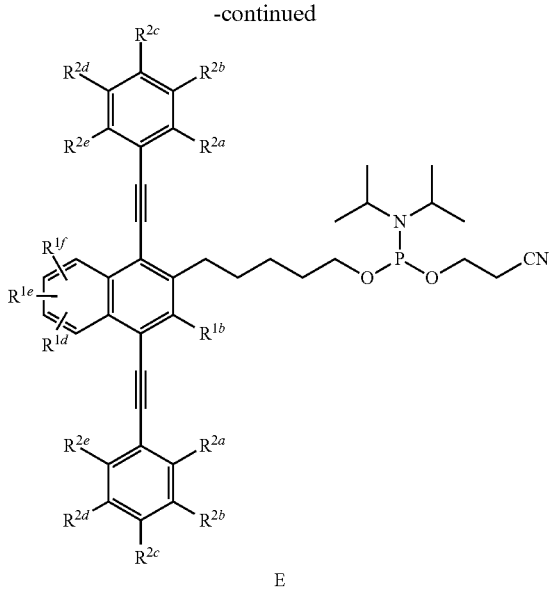

E

Reaction Scheme I illustrates an exemplary method for preparing an exemplary compound of structure (I). Referring to Reaction Scheme 1, compounds of structure A and B can be purchased or prepared by methods well-known to those of ordinary skill in the art. Treatment of 2 equivalents of A with a strong base, such as n-butyl lithium, followed by reaction with B results in compounds of structure C. Compounds of structure C can be further functionalized by reaction with 9-BBN and an appropriate precursor to linking moiety $L^1$ to produce compounds of structure D. Compound D is then functionalized with the desired $R^3$ moiety. General Reaction Scheme I illustrates a compound of structure (I) comprising a phosphoramidite (compound E) in the $R^3$ position, but other compounds of structure (I) having different $R^3$ moieties are prepared via an analogous manner.

Although General Reaction Scheme I depicts preparation of symmetrical (i.e., identical phenyl groups) compounds of structure (I), it will be readily apparent to one of ordinary skill in the art that other, non-symmetrical, compounds of structure (I) can be prepared by similar methods (e.g., stepwise reaction of differently substituted phenyls). It should also be noted that General Reaction Scheme I illustrates a compound of structure (I) wherein $L^1$ is an alkylene linker, but other compounds of structure (I) with different linking moieties or no linking moiety are prepare via analogous methods.

Further, compounds of structure (I) obtained by the above methods can be further modified to obtain different compounds of structure (I). For example, in certain embodiments phosphoramidite E is further functionalized using common techniques (e.g., techniques analogous to solid-phase DNA synthesis) to obtain compounds of structure (I) comprising various $R^3$ moieties. Reactive moieties (M) are attached to the $R^3$ moiety using techniques known in the art and described in more detail in the examples.

Analyte molecules (e.g., biomolecules) can be attached via an optional $L^2$ linker by any one of many common methods. For example, embodiments of the compounds of structure (I) include M groups capable of forming covalent bonds with a functional group on an analyte molecule as a means for attaching analyte molecules. In certain embodiments, M groups include, but are not limited to activated phosphorus compounds (e.g., phosphoramidites), activated esters, amines, alcohols, and the like. Methods for preparation of such compounds and reacting the same with an analyte molecule to form a covalent bond are well-known in the art.

In some embodiments, the compounds of structure (I) comprise a covalent bond to an oligonucleotide. Such bonds may be formed by including a phosphoramidite moiety in the compound of structure (I) and reacting the same with an oligomer (or phosphoramidite monomer) under standard DNA synthesis conditions.

DNA synthesis methods are well-known in the art. Briefly, two alcohol groups are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol can be protected as a DMT group by reaction with DMT-Cl. A secondary alcohol is then functionalized as a phosphoramidite by reaction with an appropriate reagent such as 2-cyanoethyl N,N-dissopropylchlorophosphoramidite. Methods for preparation of phosphoramidites and their oligomerization are well-known in the art and described in more detail in the examples.

In still other embodiments, the compounds are useful in various analytical methods. For example, in certain embodiments the disclosure provides a method of staining a sample, the method comprising adding to said sample a compound of structure (I) in an amount sufficient to produce an optical response when said sample is illuminated at an appropriate wavelength.

In yet other embodiments of the foregoing method, M is an analyte molecule such as a biomolecule. For example, in some embodiments the biomolecule is nucleic acid, amino acid or a polymer thereof (e.g., polynucleotide or polypeptide).

In still more embodiments, the biomolecule is an enzyme, receptor, receptor ligand, antibody, glycoprotein, aptamer or prion.

In yet other embodiments of the foregoing method, M is a microparticle. For example, in some embodiments the microparticle is a polymeric bead or nonpolymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, comprising:
(a) providing a compound of structure (I), wherein M is an analyte molecule; and
(b) detecting the compound by its visible properties.

For example, in some embodiments the biomolecule is a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In other embodiments, a method for visually detecting a biomolecule is provided, the method comprising:
 (a) admixing any of the foregoing compounds with one or more biomolecules; and
 (b) detecting the compound by its visible properties.

For example, in some embodiments the compound admixed with the one or more biomolecules will be a compound of structure (I) wherein M is a reactive moiety, and in further embodiments the reactive moiety forms a covalent bond or other strong association with the biomolecule.

As noted above, certain embodiments of the compounds of structure (I) comprise an analyte molecule (e.g., biomolecule) or a ligand attached (conjugated) thereto. Attachment may be, for example, by covalent bonding, ionic bonding, dated bonding, hydrogen bonding, and other forms of molecular bonding.

Several types of analyte molecules are suitable for conjugation to the compounds of structure (I). For example, useful conjugated substrates of the invention include, but are not limited to, compounds of structure (I) comprising an analyte molecule attached thereto (also referred to herein as a "conjugated substrate"), the analyte molecule being selected from antigens, small molecules, steroids, vitamins, drugs, haptens, metabolites, toxins, environmental pollutants, amino acids, peptides, proteins, photosensitizers, nucleotides, oligonucleotides, nucleic acids, carbohydrates, lipids, ion-complexing moieties and non-biological polymers. In one exemplary embodiment, the conjugated substrate is a natural or synthetic amino acid, a natural or synthetic peptide or protein, or an ion-complexing moiety. Exemplary peptides include, but are not limited to protease substrates, protein kinase substrates, phosphatase substrates, neuropeptides, cytokines, and toxins. Exemplary protein conjugates include enzymes, antibodies, lectins, glycoproteins, histones, alumin, lipoproteins, avidin, streptavidins, protein A, protein G, casein, phycobiliproteins, other fluorescent proteins, hormones, toxins, growth factors, and the like.

The point of attachment of the analyte molecule to the remainder of the compound of structure (I) can and will vary depending upon the embodiment. Further, some embodiments include a linker ($L^2$) between the analyte molecule and the remainder of the compound of structure (I), although use of the linker is optional and not required in all embodiments. It is also envisioned that the compound of structure (I) may comprise more than one analyte molecule. For example, two, three or more than three analyte molecules may be conjugated to the naphthyl and/or phenyl rings of compound (I).

Several methods of linking dyes to various types of analyte molecules are well known in the art. For example, methods for conjugating dyes to an analyte molecule are described in R. Haugland, The Handbook: A Guide to Fluorescent Probes and Labeling Technologies, 9th Ed., 2002, Molecular Probes, Inc., and the references cited therein; and Brindley, 1992, Bioconjugate Chem. 3:2, which are all incorporated herein by reference. By way of example, a compound of the disclosure may include a covalent bond to DNA or RNA via one or more purine or pyrimidine bases through an amide, ester, ether, or thioether bond; or is attached to the phosphate or carbohydrate by a bond that is an ester, thioester, amide, ether, or thioether. Alternatively, a compound of structure (I) may be bound to the nucleic acid by chemical post-modification, such as with platinum reagents, or using a photoactivatable molecule such as a conjugated psoralen.

The compounds of the invention are useful in many applications including those described for other dyes in U.S. Pat. Nos. 7,172,907; 5,268,486; and U.S. Patent Application Nos. 20040014981; and 20070042398, all of which are incorporated herein by reference in their entireties. For example, fluorescent dyes, such as those described herein, may be used in imaging with techniques such as those based on fluorescence detection, including but not limited to fluorescence lifetime, anisotropy, photoinduced electron transfer, photobleaching recovery, and non-radioactive transfer. The compounds of structure (I), as such, may be utilized in all fluorescent-based imaging, microscopy, and spectroscopy techniques including variations on such. In addition, they may also be used for photodynamic therapy and in multimodal imaging. Exemplary fluorescence detection techniques include those that involve detecting fluorescence generated within a system. Such techniques include, but are not limited to, fluorescence microscopy, fluorescence activated cell sorting (FACS), fluorescent flow cytometry, fluorescence correlation spectroscopy (FCS), fluorescence in situ hybridization (FISH), multiphoton imaging, diffuse optical tomography, molecular imaging in cells and tissue, fluorescence imaging with one nanometer accuracy (FIONA), free radical initiated peptide sequencing (FRIPs), and second harmonic retinal imaging of membrane potential (SHRIMP), as well as other methods known in the art.

Alternatively, the compounds of structure (I) can be used as markers or tags to track dynamic behavior in living cells. In this regard, fluorescence recovery after photobleaching (FRAP) can be employed in combination with the subject compounds to selectively destroy fluorescent molecules within a region of interest with a high-intensity laser, followed by monitoring the recovery of new fluorescent molecules into the bleached area over a period of time with low-intensity laser light. Variants of FRAP include, but are not limited to, polarizing FRAP (pFRAP), fluorescence loss in photo-bleaching (FLIP), and fluorescence localization after photobleaching (FLAP). The resulting information from FRAP and variants of FRAP can be used to determine kinetic properties, including the diffusion coefficient, mobile fraction, and transport rate of the fluorescently labeled molecules. Methods for such photo-bleaching based techniques are described in Braeckmans, K. et al., *Biophysical Journal* 85: 2240-2252, 2003; Braga, J. et al., *Molecular Biology of the Cell* 15: 4749-4760, 2004; Haraguchi, T., *Cell Structure and Function* 27: 333-334, 2002; Gordon, G. W. et al., *Biophysical Journal* 68: 766-778, 1995, which are all incorporated herein by reference in their entireties.

Other fluorescence imaging techniques are based on non-radioactive energy transfer reactions that are homogeneous luminescence assays of energy transfer between a donor and an acceptor. Such techniques that may employ the use of the subject fluorescent dyes include, but are not limited to, FRET, FET, FP, HTRF, BRET, FLIM, FLI, TR-FRET, FLIE, smFRET, and SHREK. These techniques are all variations of FRET.

The subject compounds may be used as biosensors such as a $Ca^{2+}$ ion indicator; a pH indicator; a phosphorylation indicator, or an indicator of other ions, e.g., magnesium, sodium, potassium, chloride and halides. For example, biochemical processes frequently involve protonation and deprotonation of biomolecules with concomitant changes in the pH of the milieu. Substitution at the meso-position with different pH-sensitive groups generates a variety of NIR fluorescent pH sensors with different pKa's. To be effective, the substituents at the meso-position will be in extended π-conjugation with the fluorophore core to effect marked spectral changes in response to different pH environments.

Uses of the disclosed compounds are in no way limited to analytical methods. In various embodiments, the compounds are used as colorants or dyes in various applications. In this respect, the substituents on the napthalene and/or phenyl moieties are not particularly limited provided the compound maintains its desired color and/or absorbance and/or emission properties. Selection of appropriate substituents for this purpose is within the skill of one of ordinary skill in the art.

In some embodiments the compounds disclosed herein find utility as a dye or colorant in textiles, plastics, paints and/or safety devices (e.g., reflective materials, emergency lights, glow sticks, etc.) One of ordinary skill in the art will readily recognize other uses for the disclosed compounds.

The following examples are provided for purposes of illustration, not limitation.

EXAMPLES

General Methods $^1$H NMR spectra were obtained on a JEOL 400 MHz spectrometer. $^1$H spectra were referenced against TMS. Reverse phase HPLC dye analysis was performed using a Waters Acquity UHPLC system with a 2.1 mm×50 mm Acquity BEH-C18 column held at 45° C. Mass spectral analysis was performed on a Waters/Micromass Quattro micro MS/MS system (in MS only mode) using MassLynx 4.1 acquisition software. Mobile phase used for LC/MS on dyes was 100 mM 1,1,1,3,3,3-hexafluoro-2-propanol (HFIP), 8.6 mM triethylamine (TEA), pH 8. Phosphoramidites and precursor molecules were analyzed using an Agilent Infinity 1260 UHPLC system with a diode array detector and High Performance Autosampler using an Aapptec© Spirit™ Peptide C18 column (4.6 mm×100 mm, 5 m particle size). Molecular weights for monomer intermediates were obtained using tropylium cation infusion enhanced ionization.[1] Excitation and emission profiles experiments were recorded on a Cary Eclipse spectra photometer.

All reactions were carried out in oven dried glassware under a nitrogen atmosphere unless otherwise stated. Commercially available DNA synthesis reagents were purchased from Glen Research (Sterling, Va.). Anhydrous pyridine, toluene, dichloromethane, diisopropylethyl amine, triethylamine, acetic acid, pyridine, and THF were purchased from Aldrich. All other chemicals were purchase from Aldrich or TCI and were used as is with no additional purification.

All oligonucleotide dyes were synthesized on an ABI 394 DNA synthesizer using standard protocols for the phosphoramidite based coupling approach. The chain assembly cycle for the synthesis of oligonucleotide phosphoramidates was the following: (i) detritylation, 3% trichloroaceticacid in dichloromethane, 1 min; (ii) coupling, 0.1 M phosphoramidite and 0.45 M tetrazole in acetonitrile, 10 min; (iii) capping, 0.5 M acetic anhydride in THF/lutidine, 1/1, v/v 15 s; (iv) oxidation, 0.1 M iodine in THF/pyridine/water, 10/10/1, v/v/v, 30 s.

Chemical steps within the cycle were followed by acetonitrile washing and flushing with dry argon for 0.2-0.4 min. Cleavage from the support and removal of base and phosphoramidate protecting groups was achieved by treatment with ammonia for 1 hour at room temperature. Oligonucleotide dyes were then analyzed by reverse phase HPLC as described above.

Example 1

Synthesis of a 9,10-Substituted Anthracene Dye Phosphoramidite Monomer (3)

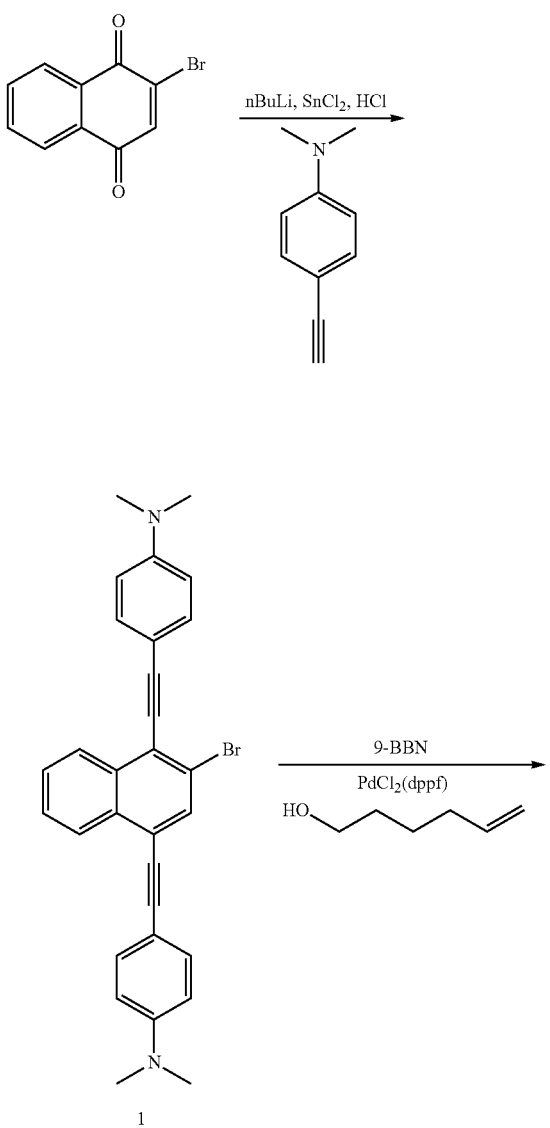

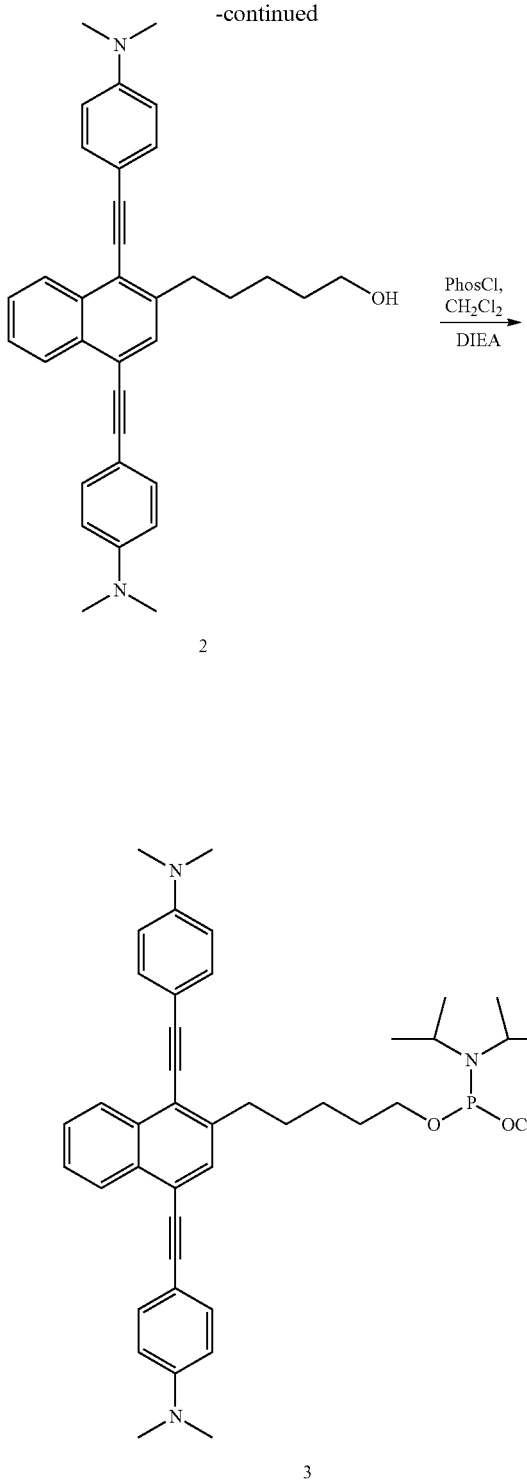

2

3

Compound 3 was prepared according to the above scheme. Further compounds of structure (I) are prepared from compound 3 using reagents and techniques known in the art.

NMR and mass spectral properties are determined using techniques known in the art, including those described above.

All of the U.S. patents, U.S. patent application publications, U.S. patent applications, foreign patents, foreign patent applications and non-patent publications referred to in this specification, including U.S. provisional patent application Ser. No. 62/121,394, filed Feb. 26, 2015, are incorporated herein by reference, in their entireties to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure

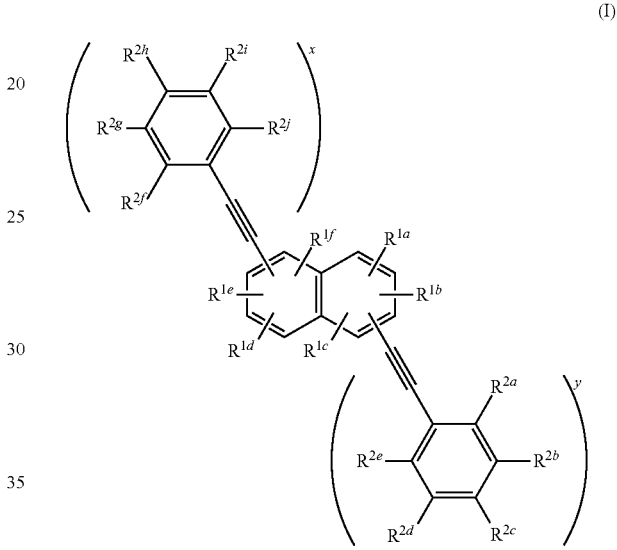

(I)

or a salt thereof, wherein:

$R^{1a}$ is -$L^1$-$(R^3)_z$-$L^2$-M or -$L^1$-$(R^3)_z$-$L^2$—S—S—$L^2$-$(R^3)_z$-$L^1$—I, where I is, independently, a further compound of structure (I);

$R^{1b}$, $R^{1c}$, $R^{1d}$, $R^{1e}$ and $R^{1f}$ are each independently H, halo, nitro, $C_1$-$C_6$ alkyl, —$SO_3^-$, —$SO_3$alkyl, $C_1$-$C_6$ alkoxy, aryl, aryloxy, $C_1$-$C_6$ alkylcarbonyl, $C_1$-$C_6$ alkylcarbonyloxy, arylcarbonyl, arylcarbonyloxy, amino, alkylamino, arylamino, aralkylamino, -$L^1$-$(R^3)_z$-$L^2$-M or -$L^1$-$(R^3)_z$-$L^2$—S—S—$L^2$-$(R^3)_z$-$L^1$—I, where I is, independently, a further compound of structure (I); or one of $R^{1a}$, $R^{1b}$, $R^{1c}$, $R^{1d}$, $R^{1e}$ or $R^{1f}$ joins with another one of $R^{1a}$, $R^{1b}$, $R^{1c}$, $R^{1d}$, $R^{1e}$ or $R^{1f}$ to form a carbocyclic or heterocyclic ring and the remaining $R^{1a}$, $R^{1b}$, $R^{1c}$, $R^{1d}$, $R^{1e}$ and $R^{1f}$ are each independently H, halo, nitro, $C_1$-$C_6$ alkyl, —$OSO_2^-$, —$OSO_2$alkyl, $C_1$-$C_6$ alkoxy, aryl, aryloxy, $C_1$-$C_6$ alkylcarbonyl, $C_1$-$C_6$ alkylcarbonyloxy, arylcarbonyl, arylcarbonyloxy, amino, alkylamino, arylamino, or aralkylamino;

$R^{2a}$, $R^{2b}$, $R^{2c}$, $R^{2d}$, $R^{2e}$, $R^{2f}$, $R^{2g}$, $R^{2h}$, $R^{2i}$ and $R^{2j}$ are each independently H, halo, $C_1$-$C_6$ alkoxy, aryloxy, amino, alkylamino, arylamino, aralkylamino, or heterocyclyl; or one or more of $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$ join with another one or more of $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$ on the same ring to form a mono or fused bicyclic carbocyclic or heterocyclic ring and the remaining $R^{2a}$, $R^{2b}$, $R^{2c}$, $R^{2d}$, $R^{2e}$, $R^{2f}$, $R^{2g}$, $R^{2h}$, $R^{2i}$ and $R^{2j}$ are each independently H, halo, $C_1$-$C_6$ alkoxy, aryloxy, amino, alkylamino, arylamino, aralkylamino, or heterocyclyl;

$R^3$ is, at each occurrence, independently a mono or bivalent functional group selected from the group consisting of polyalkylether, polyalkylenether, hydroxylalkoxy, hydroxylalkyl, hydroxylalkylene, aminoalkylene, aminoalkoxy, hydroxylpolyalkylether, hydroxylpolyalkylenether, aminopolyalkylether, aminopolyalkylenether, phosphate, thiophosphate, phospho, thiophospho, phosphoalkyl, phosphoalkylene, phosphoalkylether, thiophosphoalkyl, thiophosphoalkylene, thiophosphoalkylether, phosphoramidite and activated phosphorous;

M is sulfhydryl, disulfide, an activated ester, isothiocyanate, azide, alkyne, alkene, diene, dienophile, acid halide, sulfonyl halide, phosphine, α-haloamide, biotin, amino or a maleimide; or M is an analyte molecule or solid support;

$L^1$ and $L^2$ are, at each occurrence, independently an optional linker;

x and y are each independently an integer from 0 to 4, and the sum of x and y is 2 or greater; and z is an integer from 1 to 10.

2. The compound of claim 1, wherein the sum of x and y is 2.

3. The compound of claim 1, wherein x is 0 and y is 2.

4. The compound of claim 1, wherein the compound has the following structure (Ia):

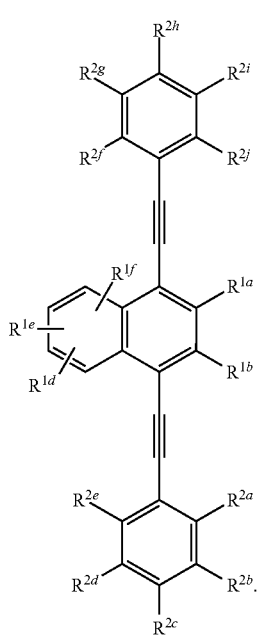

(Ia)

5. The compound of claim 4, wherein the compound has the following structure (Ia'):

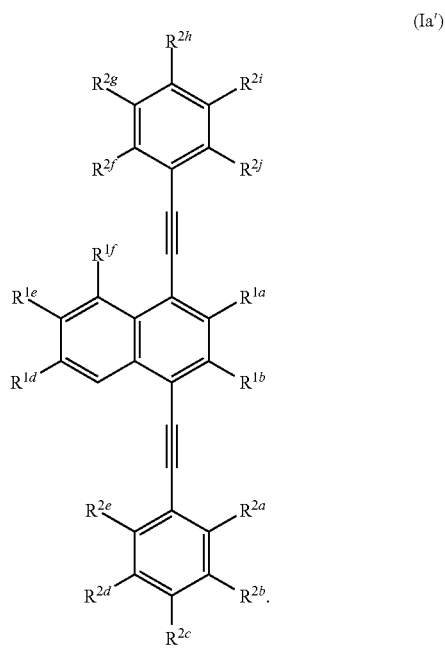

(Ia')

6. The compound of claim 1, wherein $R^{1a}$ is -$L^1$-$(R^3)_z$-$L^2$-M.

7. The compound of claim 1, wherein at least one of $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$ is amino, alkylamino, arylamino, aralkylamino or heterocyclyl.

8. The compound of claim 1, wherein one or more of $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$ join with another one or more of $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$ on the same ring to form a mono or fused bicyclic carbocyclic or heterocyclic ring and the remaining $R^{2a}$, $R^{2b}$, $R^{2c}$, $R^{2d}$, $R^{2e}$, $R^{2f}$, $R^{2g}$, $R^{2h}$, $R^{2i}$ and $R^{2j}$ are each independently H, halo, $C_1$-$C_6$ alkoxy, aryloxy, amino, alkylamino, arylamino, aralkylamino, or heterocyclyl.

9. The compound of claim 8, wherein the compound has one of the following structures:

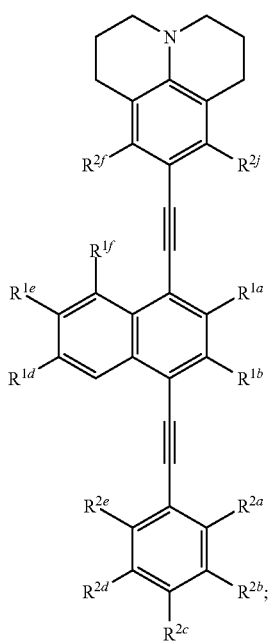
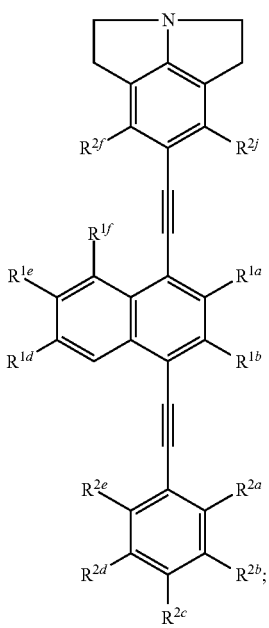
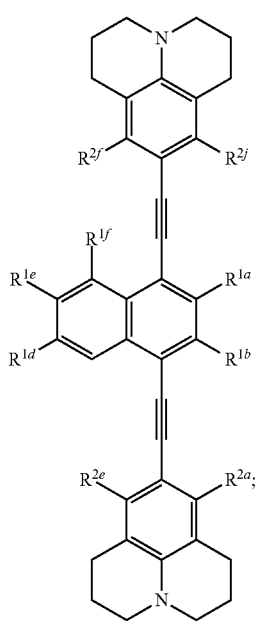
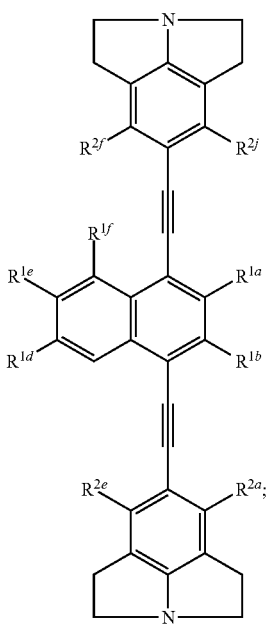

61
-continued
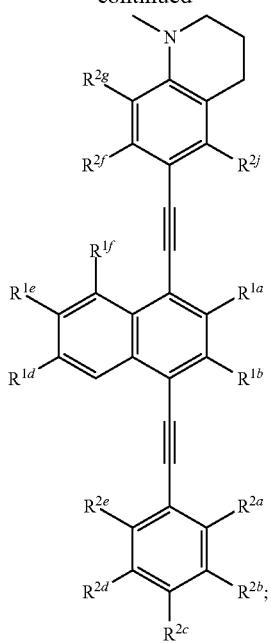
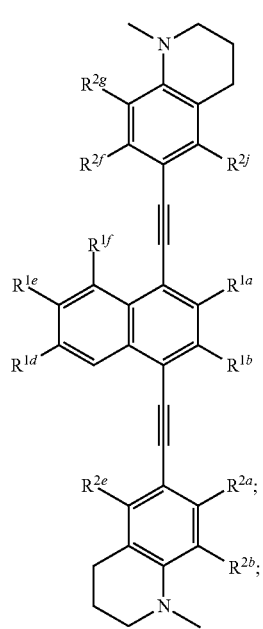
62
-continued
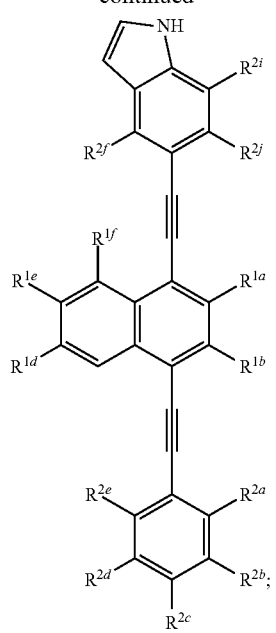
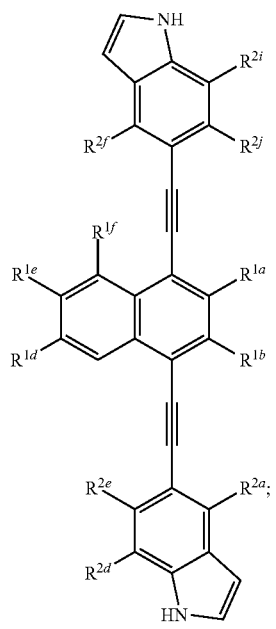

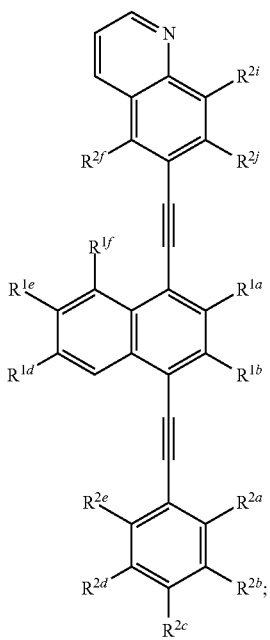

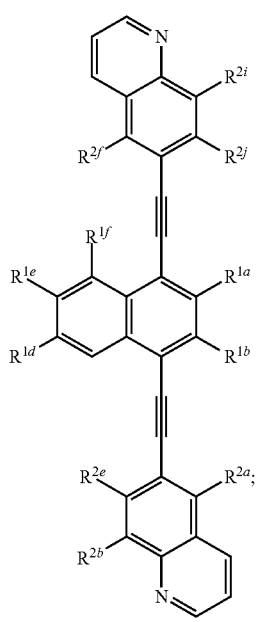

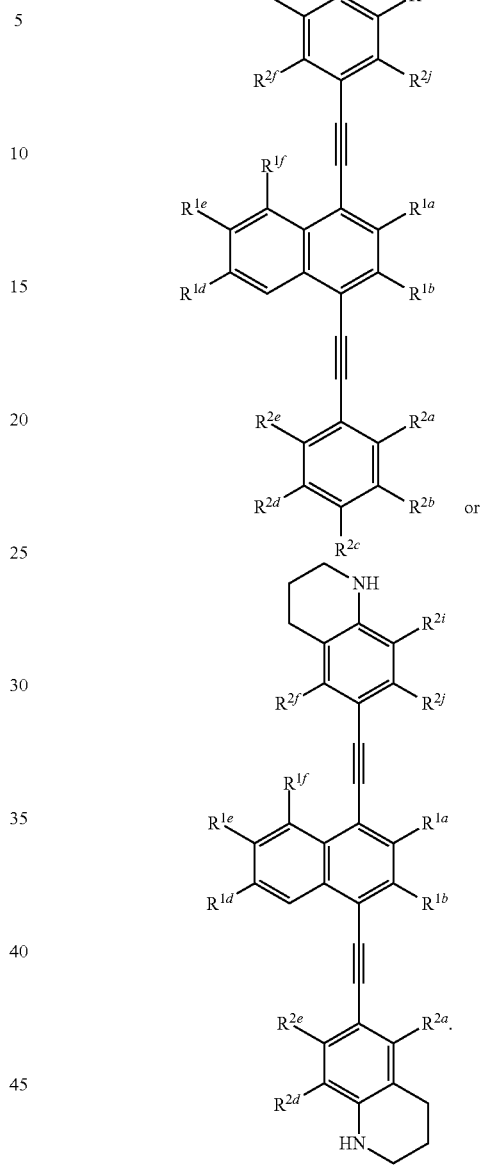

10. The compound claim 1, wherein at least one of $R^{2a}$, $R^{2b}$, $R^{2c}$, $R^{2d}$, $R^{2e}$, $R^{2f}$, $R^{2g}$, $R^{2i}$ or $R^{2j}$ is halo, alkoxy or aryloxy.

11. The compound of claim 1, wherein each of $R^{2a}$, $R^{2b}$, $R^{2d}$, $R^{2e}$, $R^{2f}$, $R^{2g}$, $R^{2i}$ and $R^{2j}$ is H.

12. The compound of claim 1, wherein $R^{1b}$, $R^{1c}$, $R^{1d}$, $R^{1e}$ and $R^{1f}$ are each independently H, halo, nitro, $C_1$-$C_6$ alkyl, —$SO_3^-$, —$SO_3$alkyl, $C_1$-$C_6$ alkoxy, aryl, aryloxy, $C_1$-$C_6$ alkylcarbonyl, $C_1$-$C_6$ alkylcarbonyloxy, arylcarbonyl, arylcarbonyloxy, amino, alkylamino, arylamino, or aralkylamino.

13. The compound of claim 1, wherein one of $R^{1b}$, $R^{1c}$, $R^{1d}$, $R^{1e}$ or $R^{1f}$ joins with another one of $R^{1b}$, $R^{1c}$, $R^{1d}$, $R^{1e}$ or $R^{1f}$ to form a carbocyclic or heterocyclic ring and the remaining $R^{1b}$, $R^{1c}$, $R^{1d}$, $R^{1e}$ and $R^{1f}$ are each independently H, halo, nitro, $C_1$-$C_6$ alkyl, —$OSO_2^-$, —$OSO_2$alkyl, $C_1$-$C_6$ alkoxy, aryl, aryloxy, $C_1$-$C_6$ alkylcarbonyl, $C_1$-$C_6$ alkylcarbonyloxy, arylcarbonyl, arylcarbonyloxy, amino, alkylamino, arylamino, or aralkylamino.
14. The compound of claim 1, wherein the compound has one of the following structures:
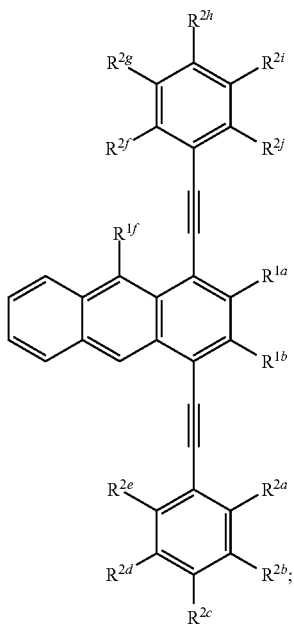
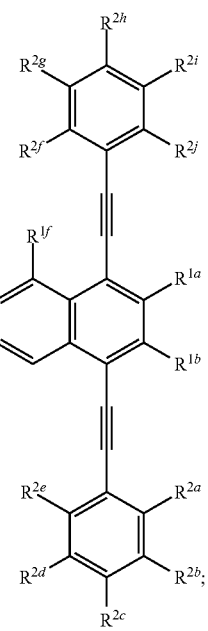
-continued
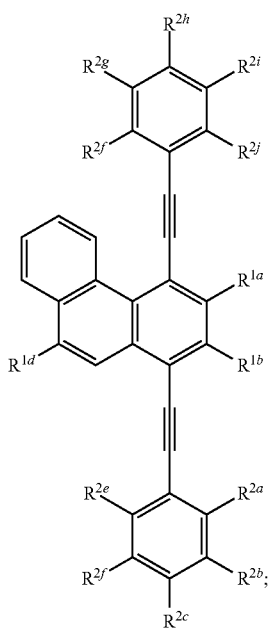
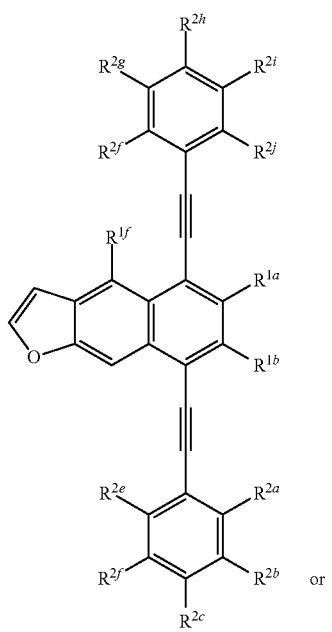
or -continued

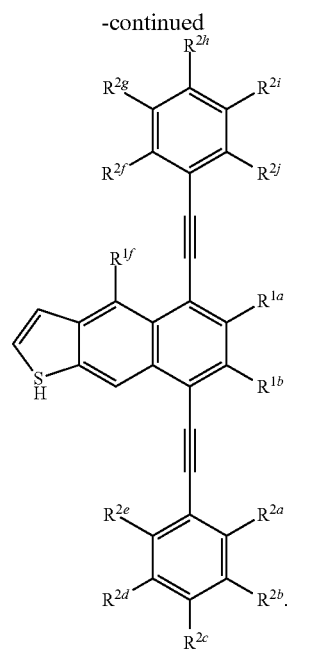

15. The compound of claim 1, wherein -(R$^3$)$_z$-L$^2$-M has one of the following structures:

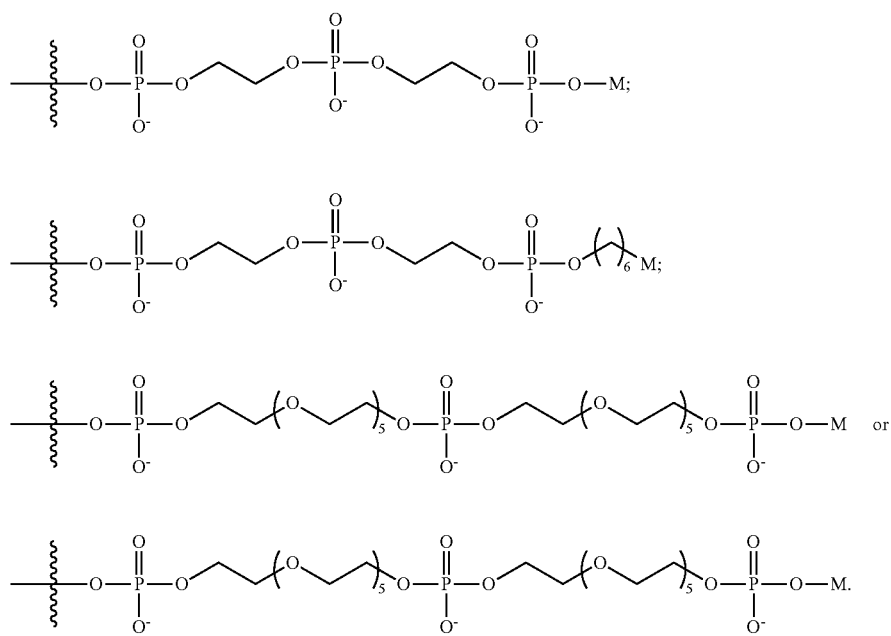

16. The compound of claim 1, wherein R$^3$ is phosphoramidite and M is sulfhydryl, disulfide, an activated ester, isothiocyanate, azide, alkyne, alkene, diene, dienophile, acid halide, sulfonyl halide, phosphine, α-haloamide, biotin, amino or a maleimide.

17. The compound of claim 1, wherein the activated ester comprises N-succinimide ester, imidoester or polyflourophenyl ester.

18. The compound of claim 1, wherein M is an analyte molecule or solid support.

19. A compound having one of the following structures:
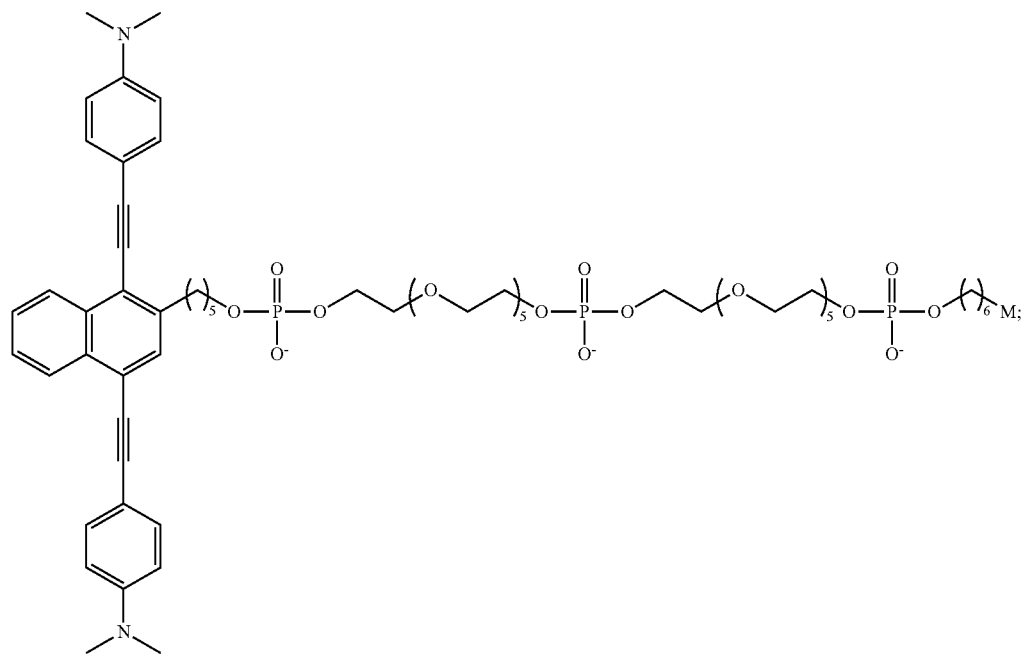
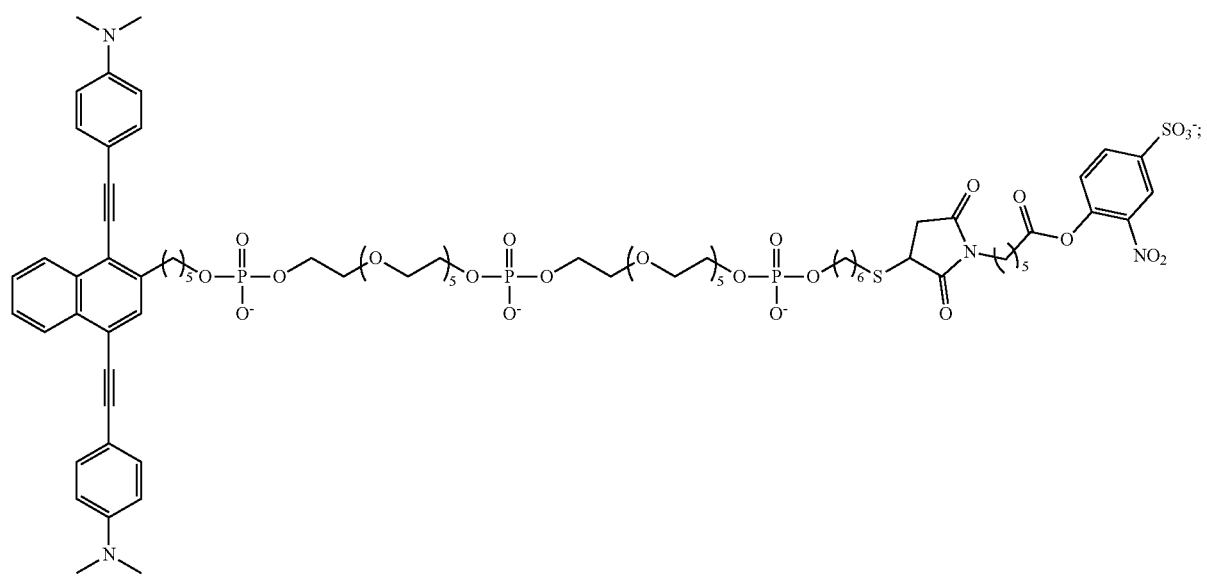

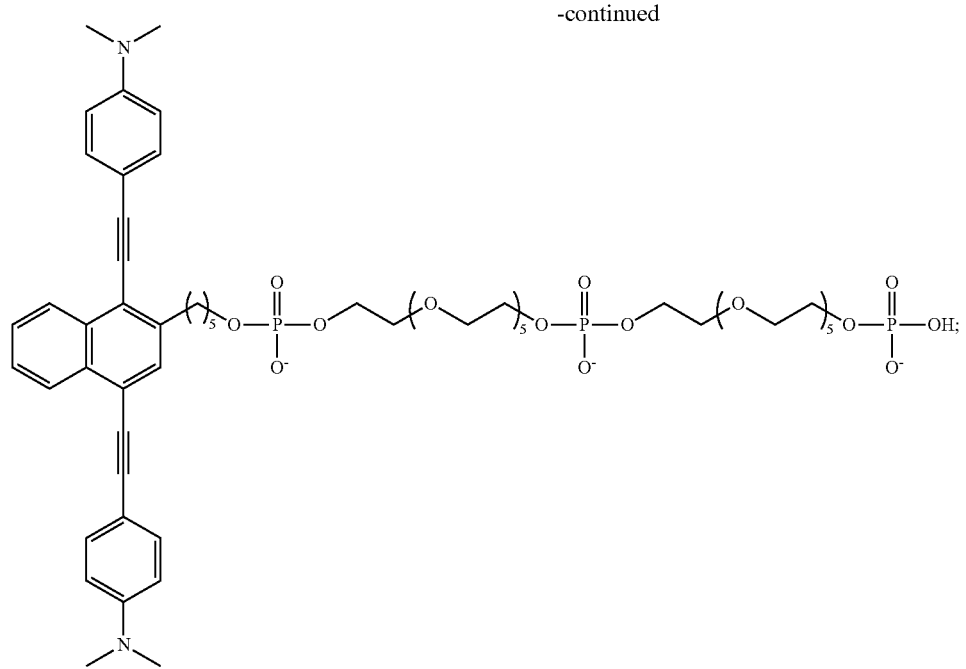
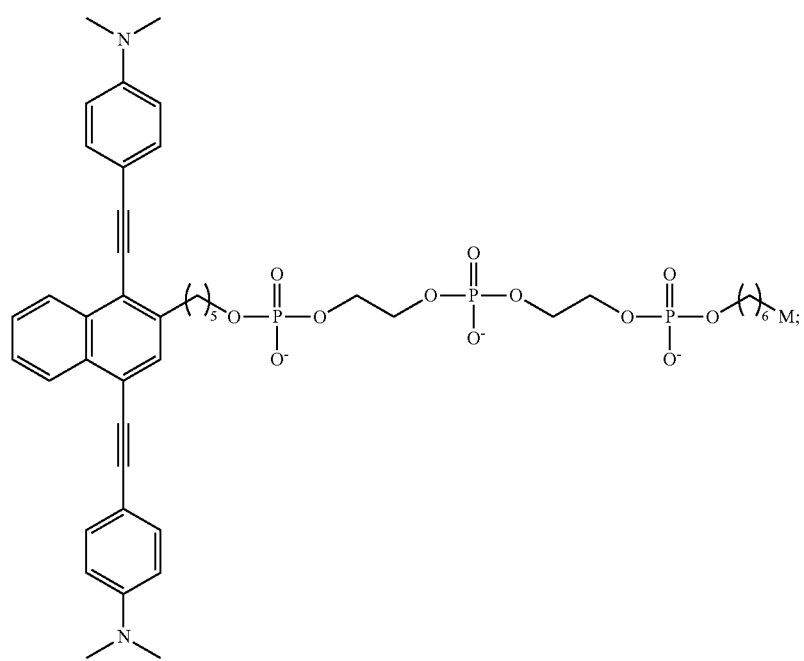

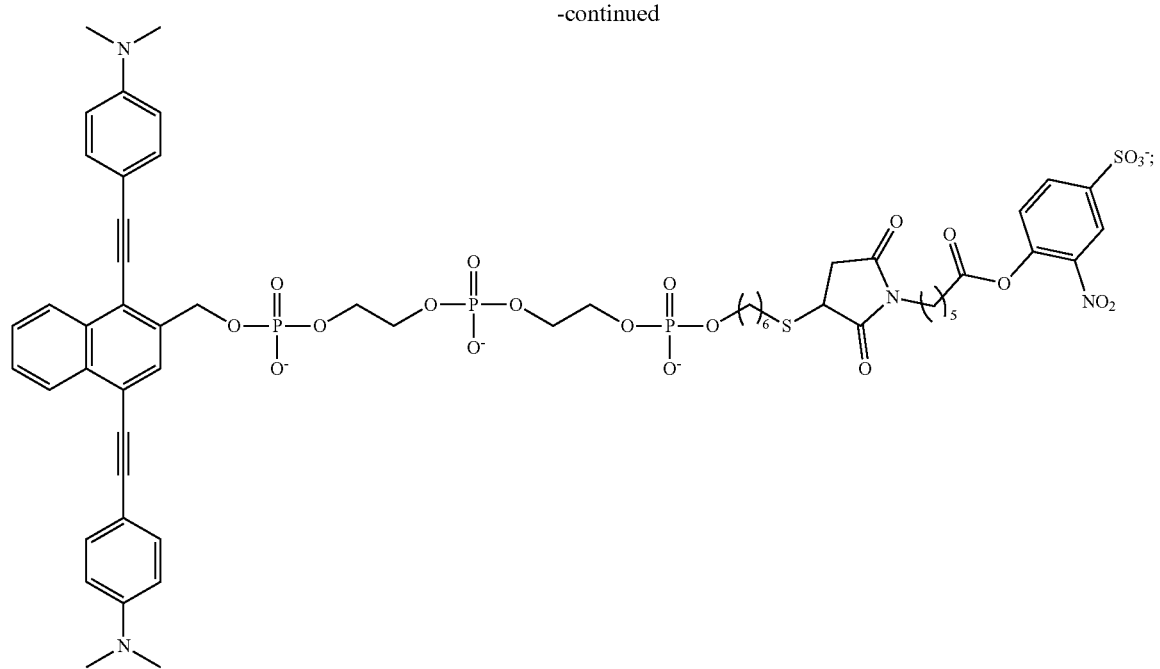
-continued
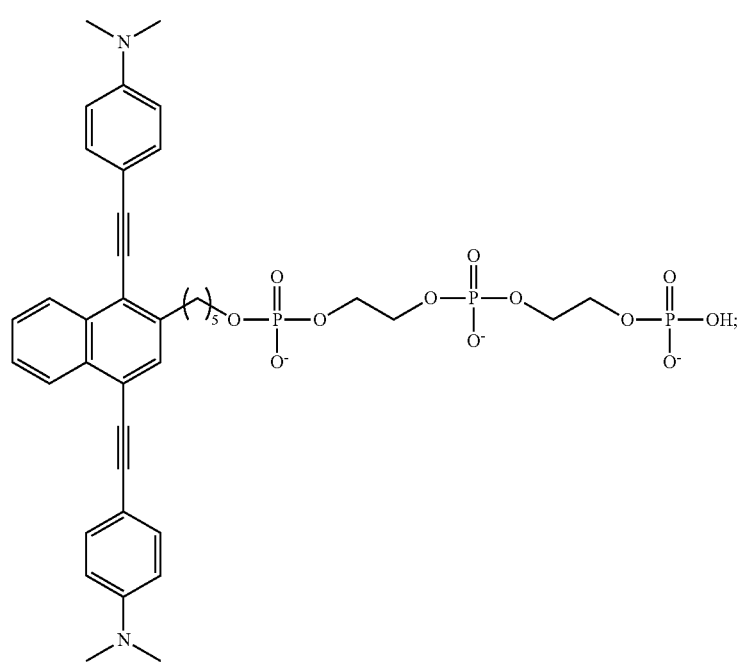

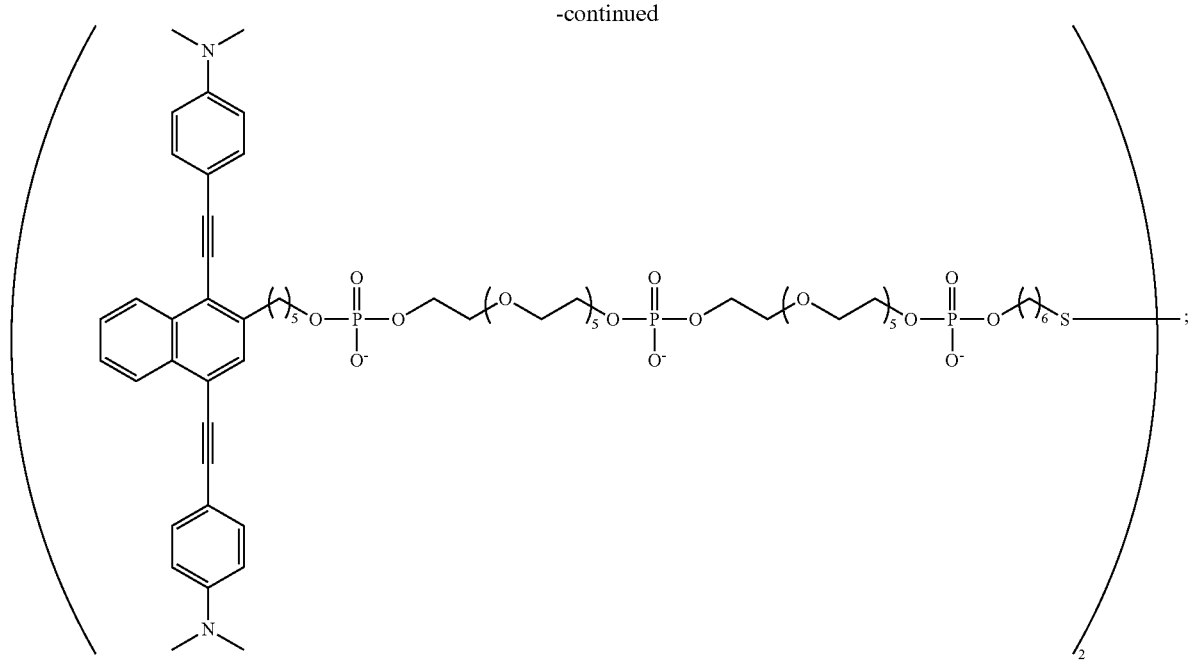
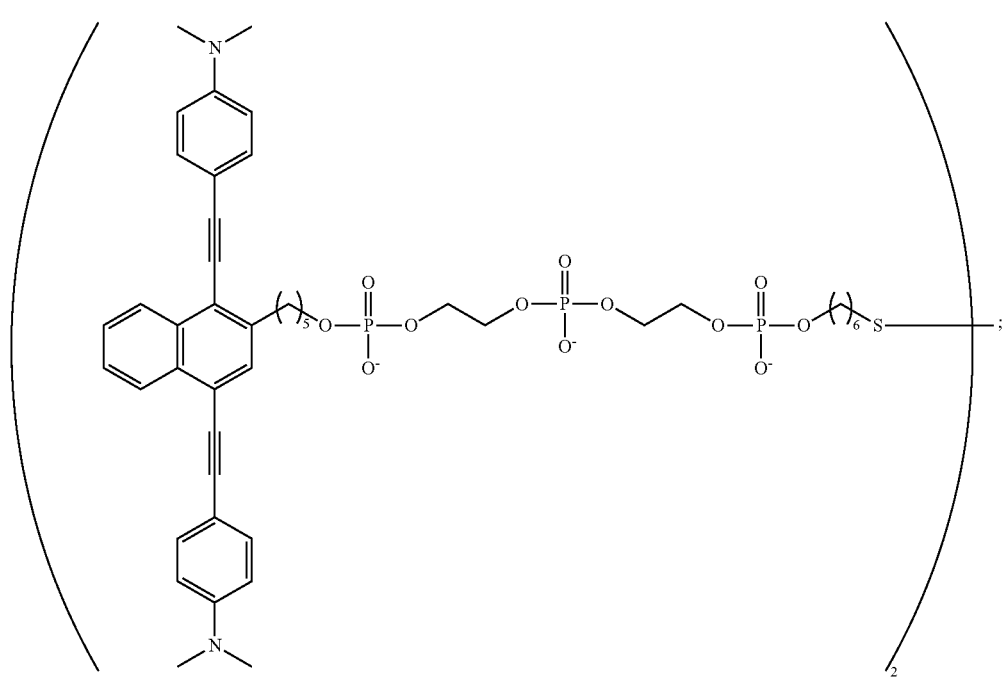

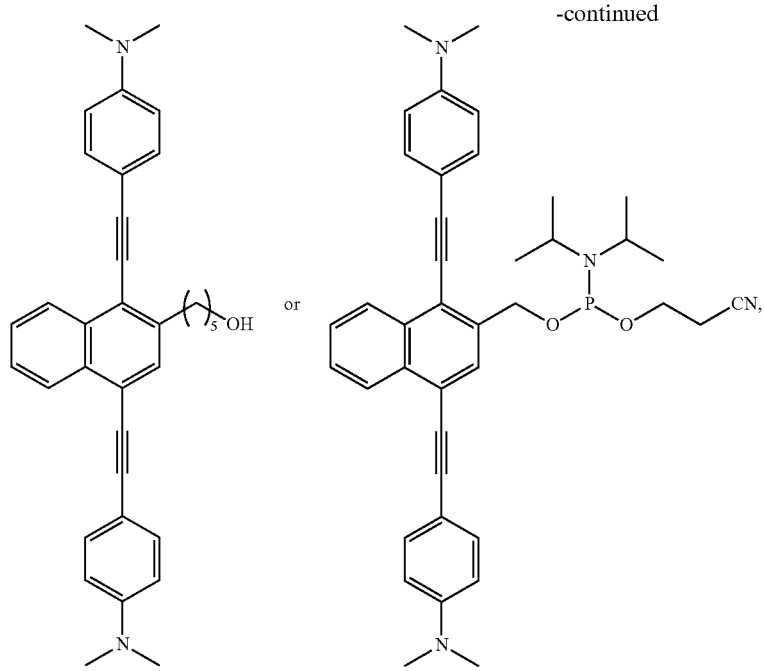

or a salt thereof, where M is H, sulfhydryl, disulfide, N-succinimide ester, imidoester, polyflourophenyl ester, isothiocyanate, azide, alkyne, alkene, diene, dienophile, acid halide, sulfonyl halide, phosphine, α-haloamide, biotin, amino or a maleimide; or M is an analyte molecule or solid support covalently linked via an optional linker.

20. A method for visually detecting a biomolecule, the method comprising:
   admixing a compound with one or more biomolecules;
   conjugating the compound with the one or more biomolecules; and
   detecting the compound conjugated to the one or more biomolecules by its visible properties,
   wherein the compound has the following structure (I):

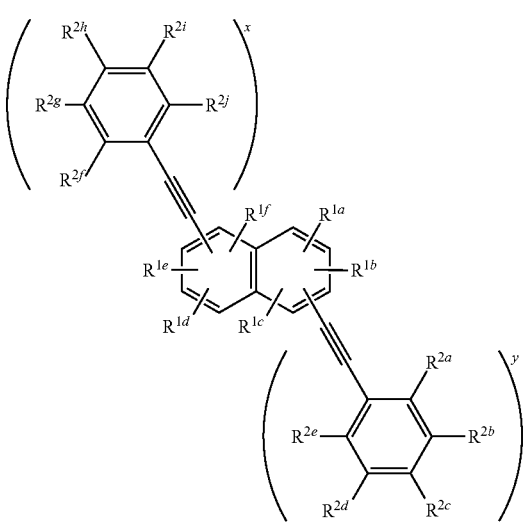

or a salt thereof, wherein:
$R^{1a}$ is -L$^1$-(R$^3$)$_z$-L$^2$-M or -L$^1$-(R$^3$)$_z$-L$^2$-(R$^3$)$_z$-L$^1$—I, where I is, independently, a further compound of structure (I);
$R^{1b}$, $R^{1c}$, $R^{1d}$, $R^{1e}$ and $R^{1f}$ are each independently H, halo, nitro, $C_1$-$C_6$ alkyl, —SO$_3^-$, —SO$_3$alkyl, $C_1$-$C_6$ alkoxy, aryl, aryloxy, $C_1$-$C_6$ alkylcarbonyl, $C_1$-$C_6$ alkylcarbonyloxy, arylcarbonyl, arylcarbonyloxy, amino, alkylamino, arylamino, aralkylamino, -L$^1$-(R$^3$)$_z$-L$^2$-M or -L$^1$-(R$^3$)$_z$-L$^2$—S—S—L$^2$-(R$^3$)$_z$-L$^1$—I, where I is, independently, a further compound of structure (I); or one of $R^{1a}$, $R^{1b}$, $R^{1c}$, $R^{1d}$, $R^{1e}$ or $R^{1f}$ with another one of $R^{1a}$, $R^{1b}$, $R^{1c}$, $R^{1d}$, $R^{1e}$ or $R^{1f}$ to form a carbocyclic or heterocyclic ring and the remaining $R^{1a}$, $R^{1b}$, $R^{1c}$, $R^{1d}$$R^{1e}$ and $R^{1f}$ are each independently H, halo, nitro, $C_1$-$C_6$ alkyl, —OSO$_2^-$, —OSO$_2$alkyl, $C_1$-$C_6$ alkoxy, aryl, aryloxy, $C_1$-$C_6$ alkylcarbonyl, $C_1$-$C_6$ alkylcarbonyloxy, arylcarbonyl, arylcarbonyloxy, amino, alkylamino, arylamino, or aralkylamino;
$R^{2a}$, $R^{2b}$, $R^{2c}$, $R^{2d}$, $R^{2e}$, $R^{2f}$, $R^{2g}$, $R^{2h}$, $R^{2i}$ and $R^{2j}$ and are each independently H, halo, $C_1$-$C_6$ alkoxy, aryloxy, amino, alkylamino arylamino, aralkylamino, or heterocycle; or one or more of $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$ join with another one or more of $R^{2a}$, $R^{2b}$, $R^{2c}$, $R^{2d}$, $R^{2e}$, $R^{2f}$, $R^{2g}$, $R^{2h}$, $R^{2i}$ or $R^{2j}$ on the same ring to form a mono or fused bicyclic carbocyclic or heterocyclic ring and the remaining $R^{2a}$, $R^{2b}$, $R^{2c}$, $R^{2d}$, $R^{2e}$, $R^{2f}$, $R^{2g}$$R^{2h}$, $R^{2i}$ and $R^{2j}$ are each independently H, halo, $C_1$-$C_6$ alkoxy, aryloxy, alkylamino, arylamino, aralkylamino, or heterocyclyl;
$R^3$ is, at each occurrence, independently a mono or bivalent functional group selected from the group consisting of polyalkylether, polyalkylenether, hydroxylalkoxy, hydroxylalkyl, hydroxyalkylene, aminoalkylene, aminoalkoxy, hydroxylpolyalkylether, hydroxylpolyalkylenether, aminopolyalkylether, aminopolyalkylenether, phosphate, thiophosphate, phospho, thiophospho, phosphoalkyl, phosphoalkylene, phosphoalkylether, thiophosphoalkyl, thiophosphoalkylene, thiophosphoalkylether, phosphoramidite and activated phosphorous;

M is sulfhydryl, disulfide, an activated ester, isothiocyanate, azide, alkyne, alkene, diene, dienophile, acid halide, sulfonyl halide, phosphine, α-haloamide, biotin, amino or a maleimide: car M is an analyte molecule or solid support;

$L^1$ and $L^2$ are, at each occurrence, independently an optional linker;

x and y are each independently an integer from 0 to 4, and the sum of x and y is 2 or greater; and z is an integer from 1 to 10.

* * * * *